(12) United States Patent
Abe

(10) Patent No.: US 7,837,625 B2
(45) Date of Patent: Nov. 23, 2010

(54) ULTRASONIC IMAGE PROCESSOR AND ULTRASONIC DIAGNOSTIC INSTRUMENT

(75) Inventor: Yasuhiko Abe, Otawara (JP)

(73) Assignees: Kabushiki Kaisha Toshiba, Tokyo (JP); Toshiba Medical System Corporation, Otawara-shi (JP)

( * ) Notice: Subject to any disclaimer, the term of this patent is extended or adjusted under 35 U.S.C. 154(b) by 1799 days.

(21) Appl. No.: 10/968,095

(22) Filed: Oct. 20, 2004

(65) Prior Publication Data

US 2005/0085729 A1    Apr. 21, 2005

(30) Foreign Application Priority Data

Oct. 21, 2003    (JP)    ............... 2003-360865

(51) Int. Cl.
A61B 8/00    (2006.01)
(52) U.S. Cl. .................................... 600/454
(58) Field of Classification Search ............... 600/450, 600/451, 453–458, 468, 407, 467, 437, 438, 600/443, 447, 462–466
See application file for complete search history.

(56) References Cited

U.S. PATENT DOCUMENTS

| | | | | |
|---|---|---|---|---|
| 5,615,680 A | * | 4/1997 | Sano | .......................... 600/437 |
| 5,622,172 A | | 4/1997 | Li et al. | |
| 5,622,174 A | * | 4/1997 | Yamazaki | .................... 600/441 |
| 5,669,387 A | | 9/1997 | Mine | |
| 5,673,700 A | | 10/1997 | Yamazaki et al. | |
| 5,701,897 A | | 12/1997 | Sano | |
| 6,638,221 B2 | | 10/2003 | Abe et al. | |
| 6,884,216 B2 | * | 4/2005 | Abe et al. | .................... 600/440 |

FOREIGN PATENT DOCUMENTS

| | | |
|---|---|---|
| JP | 6-285064 | 10/1994 |
| JP | 9-122122 | 5/1997 |
| JP | 2003-175041 | 6/2003 |

OTHER PUBLICATIONS

U.S. Appl. No. 11/336,958, filed Jan. 23, 2006, Abe.
U.S. Appl. No. 11/180,608, filed Jul. 14, 2005, Abe.
Andrew E. Arai, et al., "Myocardial Velocity Gradient Imaging by Phase Contrast MRI with Application to Regional Function in Myocardial Ischemia", Magnetic Resonance in Medicine, vol. 42, No. 1, Jul. 1999, pp. 98-109.
Y. Mine, et al., "Wall Motion Imaging Using Tissue Doppler Method", The Japan Society of Ultrasonics in Medicine's collection of works on medical theories 63, Nov. 1993, pp. 671-672.

* cited by examiner

Primary Examiner—Eric F Winakur
Assistant Examiner—Lawrence N Laryea
(74) Attorney, Agent, or Firm—Oblon, Spivak, McClelland, Maier & Neustadt, L.L.P.

(57) ABSTRACT

In a tissue tracking imaging (TTI) method, a velocity distribution image from which a translation velocity component or a rotation velocity component resulting from movement of a body, etc. is removed is generated every time phase. By tracking a predetermined position of a tissue on the basis of the velocity distribution image and generating a motion information image, it is possible to provide a diagnostic image having higher reliability.

30 Claims, 16 Drawing Sheets

ANGLE CORRECTION WITH NO MOVEMENT
OF CONTRACTION CENTER $P^t$: POSITION OF POINT P AT TIME PHASE t
$C^t$: POSITION OF CONTRACTION CENTER C AT TIME PHASE t
$V_{p:obs}^t$: OBSERVED VELOCITY AT POINT $P^t$
$V_{p:cont}^t$: CONTRACTION (EXPANSION) VELOCITY COMPONENT
OF TISSUE AT POINT $P^t$ TRACKING MOVEMENT OF CONTRACTION CENTER
(NEGLECT ADDITION OF WHOLE MOVEMENT VELOCITY)

$P^t$: POSITION OF POINT P AT TIME PHASE t
$C^t$: POSITION OF CONTRACTION CENTER C AT TIME PHASE t
$V_{p:cont}^t$: CONTRACTION (EXPANSION) VELOCITY COMPONENT OF TISSUE AT POINT $P^t$
$V_{c:trans}^t$: TRANSLATION VELOCITY COMPONENT AT POINT $C^t$

ULTRASONIC IMAGE PROCESSOR AND ULTRASONIC DIAGNOSTIC INSTRUMENT

CROSS-REFERENCE TO RELATED APPLICATIONS

This application is based upon and claims the benefit of priority from prior Japanese Patent Application No. 2003-360865, filed Oct. 21, 2003, the entire contents of which are incorporated herein by reference.

BACKGROUND OF THE INVENTION

1. Field of the Invention

The present invention relates to an ultrasonic image processor and an ultrasonic diagnostic instrument which provide information effective for medical diagnosis by estimating a velocity of a biological tissue such as cardiac muscle, etc., processing estimated velocity information, and outputting local motion information of the tissue.

2. Description of the Related Art

In general, it is very important for diagnosis of biological tissues such as cardiac muscles, etc. to objectively and quantitatively estimate functions of the tissues. Various quantitative estimation methods using a heart as a sample have been tried in a field of imaging diagnoses using ultrasonic image processors. A representative example thereof is a tissue tracking imaging (TTI) method.

In the tissue tracking imaging method, for example, as disclosed in Japanese Patent Application No. 2002-272845, parameters of local displacements and distortions obtained by integrating signals derived from velocity information while tracking positions of tissues with motion are imaged as motion information of the tissues. According to this method, images of distortions and displacements of local cardiac muscles of a heart could be formed and displayed using, for example, minor axis images, and the analysis of temporal variation of image output values at local areas is supported. In the case of using the minor axis image, an important analysis target of a heart is a thickening (variation in thickness), but in the tissue tracking imaging method, components associated with the thickening are detected and imaged through an angle correction, so that a concept or setting of a motion field toward a contraction center (contraction motion field) is utilized. In the tissue tracking imaging method, the position of the contraction center is temporally moved in consideration of influence of the translation motion (also referred to as "translation") of the whole heart and the method is applicable to the temporally-variable motion field. Therefore, the variation of the contraction center position due to the translation motion can be coped with.

However, the tissue tracking imaging method has a room for improvement as described below.

First, in the tissue tracking imaging method, for the purpose of simplification in processing, the detection of velocity components that are analysis targets is an approximation. That is, the detected velocity of a predetermined position includes an error corresponding to a velocity component of movement (that is, a translation velocity component) of a contraction center due to movement of a body. This situation will be described with reference to FIGS. 1A and 1B.

FIG. 1A is a schematic diagram of a minor axis image of a heart illustrating a conventional angle correction with no movement of a contraction center. FIG. 1B is a schematic diagram of the minor axis image of a heart illustrating a conventional tracking with movement of a contraction center.

As shown in FIG. 1A, when the velocity component of movement of the contraction center is small to be neglected, there is no problem even if the estimation of $P^t$ or $V_{p:cont}^t$ (where t is a time phase) is performed while neglecting the velocity component of movement from the viewpoint of $V_{p:cont}^t = V_{p:obs}^t / \cos\theta$.

However, as shown in FIG. 1B, when a translation motion of the whole heart exists substantially, the movement velocity component of the contraction center is added to Pt, and strictly considering, the movement velocity component $V_{c:trans}^t$ of the contraction center is added to $V_{p:obs}^t$ and thus is observed. Conventionally, since this influence is neglected, a large movement of the contraction center causes an error.

Second, there is known that the movement of the whole heart is substantially very complex and a twist motion in which the whole left ventricle is contracted to efficiently send out blood exists in systole. In the minor axis image, for example, as disclosed in "Myocardial Velocity Gradient Imaging by Phase Contrast MRI With Application to Regional Function in Myocardial Ischemia" A. E. Arai et al, Magnetic Resonance in Medicine 42: 98-109, 1999, the twist motion is detected as a rotation component and studies thereof have been advanced recently using an MRI. Therefore, when it is tried to detect only the thickening component with more accuracy, the rotation component should be considered as well as the translation component.

Conventionally, from this point of view, various methods of removing the whole movement of a heart have been studied. For example, as disclosed in "Wall Motion Imaging using Tissue Doppler method", Mine et al, Hikosy's collection of works on medical theories 63: P671-672, 1993, there is a technique of obtaining only the thickening component by modeling the movement of a heart and estimating and removing the translation component which is considered as the most surest through the method of least squares (through repeated calculation using correlation coefficients) using velocities of plural points. According to this technique, it could be expected to adaptively estimate the rotation component, but there is a serious problem in that the movement of a heart is modeled. Specifically, since large variation of velocity distribution in a cardiac muscle deviates from the model (a hypothesis that a cardiac muscle is constantly contracted and expanded), it causes an error. It is known that the velocity distribution is not constant inside the cardiac muscle. Finally, from the viewpoint of trying to analyze the local distribution of motion information inside the cardiac muscle, the above technique could not avoid contradiction.

Third, in the tissue tracking imaging method, a limit area for imaging exists and a long data processing time might be required. That is, in the tissue tracking imaging method, the velocity component of a predetermined position of a cardiac muscle is obtained using a technique based on the tissue Doppler method or a technique based on two-dimensional velocity detection (pattern matching of a received ultrasonic RF signal and a B mode signal, etc.). However, in the former, a limit of a Doppler angle exists partially, so that there exists an area of which the velocity cannot be detected in principle. On the other hand, in the latter, the limit of a Doppler angle does not exist, but a very large calculation time is required for calculating a characteristic amount as an image, so that there is a difficulty in spread for clinical application.

BRIEF SUMMARY OF THE INVENTION

The present invention is contrived in view of the above problems and it is an object of the present invention to provide an ultrasonic image processor and an ultrasonic diagnostic instrument to which an improved tissue tracking imaging (TTI) method can be applied, thereby providing motion information images having high clinical applicability and new diagnostic information.

The present invention employs the following means to accomplish the above object.

The present invention may provide an ultrasonic image processor (equal to claim 1) comprising: a storage unit for storing a plurality of ultrasonic data acquired at a plurality of time phases of a heart of a sample; a motion field setting unit for setting a motion field defining a motion direction of the heart for the plurality of ultrasonic data; a contraction center setting unit for setting a contraction center of the heart for the plurality of ultrasonic data; a first distribution image generating unit for generating a first distribution image of a motion velocity in the motion direction defined by the motion field every time phase on the basis of the plurality of ultrasonic data; a first estimation unit for estimating a translation motion component of the heart based on the contraction center of the heart at at least two continuous time phases; a second distribution image generating unit for generating a second distribution image every time phase by correcting the plurality of first distribution images on the basis of the translation motion component; a tracking point setting unit for setting a plurality of tracking points existing in a tissue region of the sample on a second distribution image at a predetermined time phase among the plurality of second distribution images; a second estimation unit for estimating corresponding points corresponding to the plurality of tracking points at each time phase on the basis of velocities of the plurality of tracking points and time intervals between the plurality of time phases in the plurality of second distribution images corresponding to the other time phases other than the predetermined time phase; a signal value determining unit for determining signal values of the tracking points and the corresponding points on the basis of the second distribution image at each time phase; a motion information image generating unit for generating a motion information image on the basis of the signal values of the tracking points and the corresponding points; and a display unit for displaying the motion information image.

The present invention may provide an ultrasonic image processor (equal to claim 12) comprising: a storage unit for storing first ultrasonic data as a tissue image radiographed in a tissue Doppler mode at each of a plurality of time phases of a heart of a sample and second ultrasonic data as a tissue image radiographed in a radiography mode other than the tissue Doppler mode at each of the plurality of time phases; a motion field setting unit for setting a motion field defining a motion direction of the heart for the plurality of first ultrasonic data and the plurality of second ultrasonic data; a contraction center setting unit for setting a contraction center of the heart for the plurality of first ultrasonic data and the plurality of second ultrasonic data; a distribution image generating unit for generating a first distribution image of a motion velocity toward the contraction center every time phase on the basis of the plurality of first ultrasonic data and generating a second distribution image of a motion velocity toward the contraction center every time phase on the basis of the plurality of second ultrasonic data; a first estimation unit for estimating a translation motion component of the heart based on the contraction center of the heart at at least two continuous time phases; a corrected distribution-image generating unit for generating a first corrected distribution image every time phase by correcting a plurality of the first distribution images on the basis of the translation motion component and generating a second corrected distribution image every time phase by correcting a plurality of the second distribution images on the basis of the translation motion component; a motion information image generating unit for generating a motion information image using the first corrected distribution image and the second corrected distribution image; and a display unit for displaying the motion information image.

The present invention may provide an ultrasonic image processor (equal to claim 23) comprising: a storage unit for storing a plurality of ultrasonic data acquired at a plurality of time phases of a heart of a sample; a motion field setting unit for setting a motion direction of the heart for the plurality of ultrasonic data; a contraction center setting unit for setting a contraction center of the heart for the plurality of ultrasonic data; a first distribution image generating unit for generating a first distribution image of a motion velocity toward the contraction center along the motion direction every time phase on the basis of the plurality of ultrasonic data; a first estimation unit for estimating a translation motion component of the heart on the basis of the contraction center of the heart at at least two continuous time phases; a second distribution image generating unit for generating a second distribution image every time phase by correcting a plurality of the first distribution images on the basis of the translation motion component; a tracking point setting unit for setting a plurality of tracking points existing in a tissue region of the sample on the second distribution image at a predetermined time phase among the plurality of second distribution images; a second estimation unit for estimating corresponding points corresponding to the plurality of tracking points at each time phase on the basis of motion velocities of the plurality of tracking points and time intervals between the plurality of time phases in the plurality of second distribution images corresponding to the other time phases other than the predetermined time phase; a signal value determining unit for determining signal values of the tracking points and the corresponding points on the basis of the second distribution image at each time phase; a motion information image generating unit for generating a motion information image on the basis of the signal values of the tracking points and the corresponding points; and a display unit for displaying the motion information image.

The present invention may provide an ultrasonic image processor (equal to claim 24) comprising: a storage unit for storing first ultrasonic data as a tissue image radiographed in a tissue Doppler mode at each of a plurality of time phases of a heart of a sample and second ultrasonic data as a tissue image radiographed in a radiography mode other than the tissue Doppler mode at each time phase; a motion field setting unit for setting a motion direction of the heart for the plurality of first ultrasonic data and the plurality of second ultrasonic data; a contraction center setting unit for setting a contraction center of the heart for the plurality of first ultrasonic data and the plurality of second ultrasonic data; a distribution image generating unit for generating a first distribution image of a motion velocity toward the contraction center along the motion direction every time phase on the basis of the plurality of first ultrasonic data and generating a second distribution image of a motion velocity toward the contraction center every time phase on the basis of the plurality of second ultrasonic data; a first estimation unit for estimating a translation motion component of the heart based on the contraction center of the heart at at least two continuous time phases; a corrected distribution-image generating unit for generating a first corrected distribution image every time phase by correcting a plurality of the first distribution images on the basis of the translation motion component and generating a second corrected distribution image every time phase by correcting a plurality of the second distribution images on the basis of the translation motion component; a motion information image generating unit for generating a motion information image using the first corrected distribution image and the second corrected distribution image; and a display unit for displaying the motion information image.

The present invention may provide an ultrasonic diagnostic instrument (equal to claim 25) comprising: an ultrasonic probe for transmitting an ultrasonic wave to an area including a heart of a sample and receiving an echo signal from the sample; a driving signal generating unit for generating a driving signal driving the ultrasonic probe and applying the driving signal to the ultrasonic probe at each of a plurality of time phases of the heart of the sample; a data generating unit for generating a plurality of ultrasonic data on the basis of the echo signal received through the ultrasonic probe from the area at each of the plurality of time phases; a motion field setting unit for setting a motion field defining a motion direction of the heart for the plurality of ultrasonic data; a contraction center setting unit for setting a contraction center of the heart for the plurality of ultrasonic data; a first distribution image generating unit for generating a first distribution image of a motion velocity in the motion direction defined by the motion field every time phase on the basis of the plurality of ultrasonic data; a first estimation unit for estimating a translation motion component of the heart on the basis of the contraction center of the heart at at least two continuous time phases; a second distribution image generating unit for generating a second distribution image every time phase by correcting a plurality of the first distribution images on the basis of the translation motion component; a tracking point setting unit for setting a plurality of tracking points existing in a tissue region of the sample on a second distribution image at a predetermined time phase among the plurality of second distribution images; a second estimation unit for estimating corresponding points corresponding to the plurality of tracking points at each time phase on the basis of velocities of the plurality of tracking points and time intervals between the plurality of time phases in the plurality of second distribution images corresponding to the other time phases other than the predetermined time phase; a signal value determining unit for determining signal values of the tracking points and the corresponding points on the basis of the second distribution image at each time phase; a motion information image generating unit for generating a motion information image on the basis of the signal values of the tracking points and the corresponding points; and a display unit for displaying the motion information image.

The present invention may provide an ultrasonic diagnostic instrument (equal to claim 26) comprising: a radiography unit for acquiring first ultrasonic data as a tissue image in a tissue Doppler mode at each of a plurality of time phases of a heart of a sample and second ultrasonic data as a tissue image in a radiography mode other than the tissue Doppler mode at each of the plurality of time phases; a motion field setting unit for setting a motion field defining a motion direction of the heart for the plurality of first ultrasonic data and the plurality of second ultrasonic data; a contraction center setting unit for setting a contraction center of the heart for the plurality of first ultrasonic data and the plurality of second ultrasonic data; a distribution image generating unit for generating a first distribution image of a motion velocity toward the contraction center every time phase on the basis of the plurality of first ultrasonic data and generating a second distribution image of a motion velocity toward the contraction center every time phase on the basis of the plurality of second ultrasonic data; a first estimation unit for estimating a translation motion component of the heart based on the contraction center of the heart at at least two continuous time phases; a corrected distribution-image generating unit for generating a first corrected distribution image every time phase by correcting a plurality of the first distribution images on the basis of the translation motion component and generating a second corrected distribution image every time phase by correcting a plurality of the second distribution images on the basis of the translation motion component; a motion information image generating unit for generating a motion information image using the first corrected distribution image and the second corrected distribution image; and a display unit for displaying the motion information image.

The present invention may provide an ultrasonic image processing method (equal to claim 27) comprising: setting a motion field defining a motion direction of a heart for a plurality of ultrasonic data acquired at each of a plurality of time phases of the heart of a sample; setting a contraction center of the heart for the plurality of ultrasonic data; generating a first distribution image of a motion velocity in the motion direction defined by the motion field every time phase on the basis of the plurality of ultrasonic data; estimating a translation motion component of the heart on the basis of the contraction center of the heart at at least two continuous time phases; generating a second distribution image every time phase by correcting the plurality of first distribution images on the basis of the translation motion component; setting a plurality of tracking points existing in a tissue region of the sample on the second distribution image at a predetermined time phase among the plurality of second distribution images; estimating corresponding points corresponding to the plurality of tracking points at each time phase on the basis of velocities of the plurality of tracking points and time intervals between the plurality of time phases in the plurality of second distribution images corresponding to the other time phases other than the predetermined time phase; determining signal values of the tracking points and the corresponding points on the basis of the second distribution image at each time phase; and generating a motion information image on the basis of the signal values of the tracking points and the corresponding points.

The present invention may provide an ultrasonic image processing method (equal to claim 28) comprising: setting a motion field defining a motion direction of a heart for first ultrasonic data as a tissue image radiographed in a tissue Doppler mode at each of a plurality of time phases of the heart of a sample and second ultrasonic data as a tissue image radiographed in a radiography mode other than the tissue Doppler mode at each of the plurality of time phases; setting a contraction center of the heart for a plurality of the first ultrasonic data and a plurality of the second ultrasonic data; generating a first distribution image of a motion velocity toward the contraction center every time phase on the basis of the plurality of first ultrasonic data and generating a second distribution image of a motion velocity toward the contraction center every time phase on the basis of the plurality of second ultrasonic data; estimating a translation motion component of the heart based on the contraction center of the heart at at least two continuous time phases; generating a first corrected distribution image every time phase by correcting a plurality of the first distribution images on the basis of the translation motion component and generating a second corrected distribution image every time phase by correcting a plurality of the second distribution images on the basis of the translation motion component; and generating a motion information image using the first corrected distribution image and the second corrected distribution image.

The present invention may provide a computer-readable memory (equal to claim 29) comprising: means for causing to set a motion field defining a motion direction of a heart for a plurality of ultrasonic data acquired at each of a plurality of time phases of the heart of a sample; means for causing to set a contraction center of the heart for the plurality of ultrasonic data; means for causing to generate a first distribution image of a motion velocity in the motion direction defined by the motion field every time phase on the basis of the plurality of ultrasonic data; means for causing to estimate a translation motion component of the heart on the basis of the contraction center of the heart at at least two continuous time phases; means for causing to generate a second distribution image every time phase by correcting the plurality of first distribution images on the basis of the translation motion component; means for causing to set a plurality of tracking points existing in a tissue region of the sample on the second distribution image at a predetermined time phase among the plurality of second distribution images; means for causing to estimate corresponding points corresponding to the plurality of tracking points at each time phase on the basis of velocities of the plurality of tracking points and time intervals between the plurality of time phases in the plurality of second distribution images corresponding to the other time phases other than the predetermined time phase; means for causing to determine signal values of the tracking points and the corresponding points on the basis of the second distribution image at each time phase; means for causing to generate a motion information image on the basis of the signal values of the tracking points and the corresponding points; and means for causing to display the motion information image.

The present invention may provide a computer-readable memory (equal to claim 30) comprising: means for causing to set a motion field defining a motion direction of a heart for first ultrasonic data as a tissue image radiographed in a tissue Doppler mode at each of a plurality of time phases of the heart of a sample and second ultrasonic data as a tissue image radiographed in a radiography mode other than the tissue Doppler mode at each of the plurality of time phases; means for causing to set a contraction center of the heart for a plurality of the first ultrasonic data and a plurality of the second ultrasonic data; means for causing to generate a first distribution image of a motion velocity toward the contraction center every time phase on the basis of the plurality of first ultrasonic data and to generate a second distribution image of a motion velocity toward the contraction center every time phase on the basis of the plurality of second ultrasonic data; means for causing to estimate a translation motion component of the heart based on the contraction center of the heart at at least two continuous time phases; means for causing to generate a first corrected distribution image every time phase by correcting a plurality of the first distribution images on the basis of the translation motion component and to generate a second corrected distribution image every time phase by correcting a plurality of the second distribution images on the basis of the translation motion component; means for causing to generate a motion information image using the first corrected distribution image and the second corrected distribution image; and means for causing to display the motion information image.

The present invention may provide an ultrasonic image processor which is used for ultrasonic image diagnosis and which obtains a motion information image of a tissue on the basis of an ultrasonic echo signal from a sample and obtains a local displacement or distortion distribution image of the tissue on the basis of the motion information image and motion direction information of the tissue, the ultrasonic image processor comprising: a first unit for setting a vector field toward a contraction center of a heart as a field of the motion direction, wherein the vector field follows temporal movement of the contraction center; a second unit for obtaining a position of the contraction center of the heart; a third unit for estimating a translation motion component of the whole heart from the temporal movement of the contraction center; and a fourth unit for removing the estimated translation motion component from the detected motion information of the tissue.

The present invention may provide an ultrasonic image processor comprising: a first unit for setting a motion field defining a motion direction of a heart and a contraction center of the heart for first ultrasonic data radiographed in a tissue Doppler mode and second ultrasonic data radiographed in a radiography mode other than the tissue Doppler mode; a second unit for generating a first distribution image of a motion velocity toward the contraction center on the basis of a plurality of the first ultrasonic data and generating a second distribution image of a motion velocity toward the contraction center on the basis of a plurality of the second ultrasonic data; a third unit for estimating a translation motion component of the whole heart from temporal movement of the contraction center; a fourth unit for removing the estimated translation motion component from the first distribution image and the second distribution image; and a motion information image generating unit for generating a motion information image using the first corrected distribution image and the second corrected distribution image from which the translation motion component is removed.

The present invention may provide an ultrasonic diagnostic instrument which obtains a motion information image of a tissue on the basis of an ultrasonic echo signal from a sample and obtains a local displacement or distortion distribution image of the tissue on the basis of the motion information image and motion direction information of the tissue, the ultrasonic diagnostic instrument comprising: a first unit for setting a vector field toward a contraction center of a heart as a field of the motion direction, wherein the vector field follows temporal movement of the contraction center; a second unit for obtaining a position of the contraction center of the heart; a third unit for estimating a translation motion component of the whole heart from the temporal movement of the contraction center; and a fourth unit for removing the estimated translation motion component from the detected motion information of the tissue.

The present invention may provide an ultrasonic diagnostic instrument comprising: a first unit for setting a motion field defining a motion direction of a heart and a contraction center of the heart for first ultrasonic data radiographed in a tissue Doppler mode and second ultrasonic data radiographed in a radiography mode other than the tissue Doppler mode; a second unit for generating a first distribution image of a motion velocity toward the contraction center on the basis of a plurality of the first ultrasonic data and generating a second distribution image of a motion velocity toward the contraction center on the basis of a plurality of the second ultrasonic data; a third unit for estimating a translation motion component of the whole heart from temporal movement of the contraction center; a fourth unit for removing the estimated translation motion component from the first distribution image and the second distribution image; and a motion information image generating unit for generating a motion information image using the first corrected distribution image and the second corrected distribution image from which the translation motion component is removed.

DETAILED DESCRIPTION OF THE INVENTION

Figure 1A:
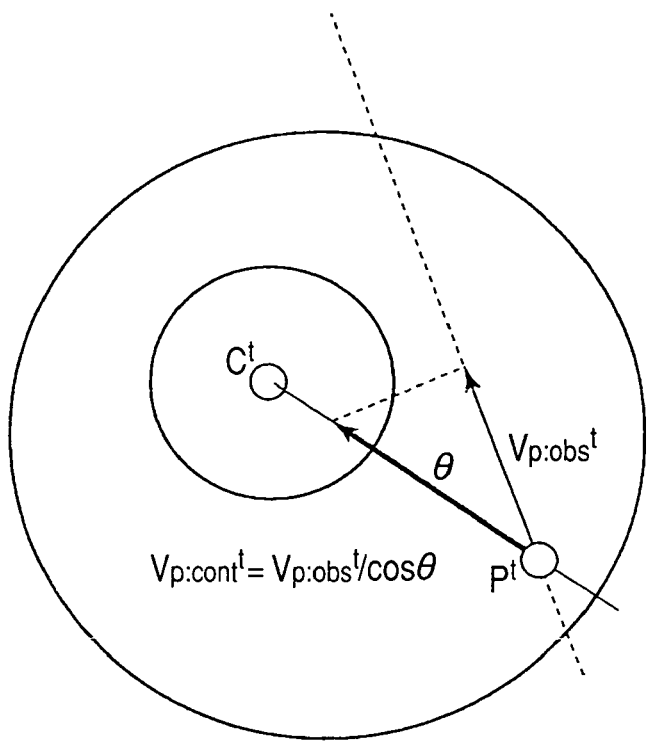
FIG. 1A is a diagram illustrating movement of a predetermined position of a cardiac muscle to explain a problem to be solved by the present invention.
Figure 1B:
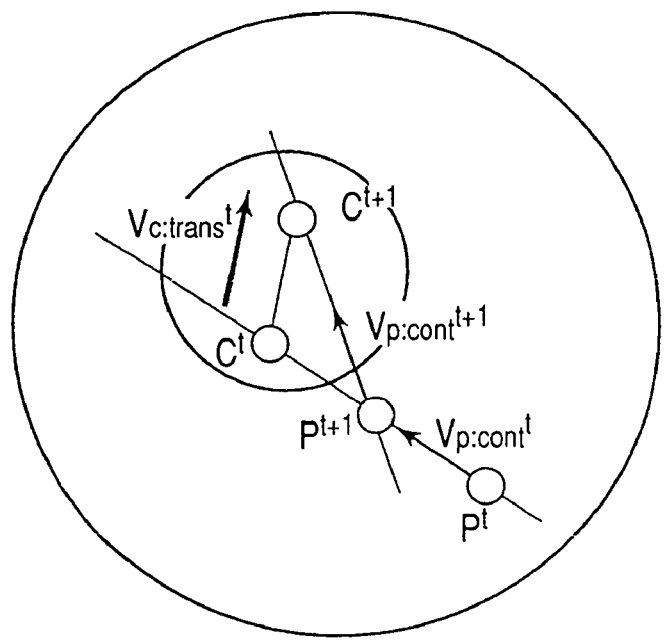
FIG. 1B is a diagram illustrating movement of a predetermined position of a cardiac muscle to explain a problem to be solved by the present invention.

Hereinafter, first to third embodiments of the present invention will be described with reference to the accompanying drawings. In the following description, constituent elements having substantially the same function and structure will be denoted by the same reference numerals and repeated description thereof will be made only as needed.

First Embodiment

Figure 2A:
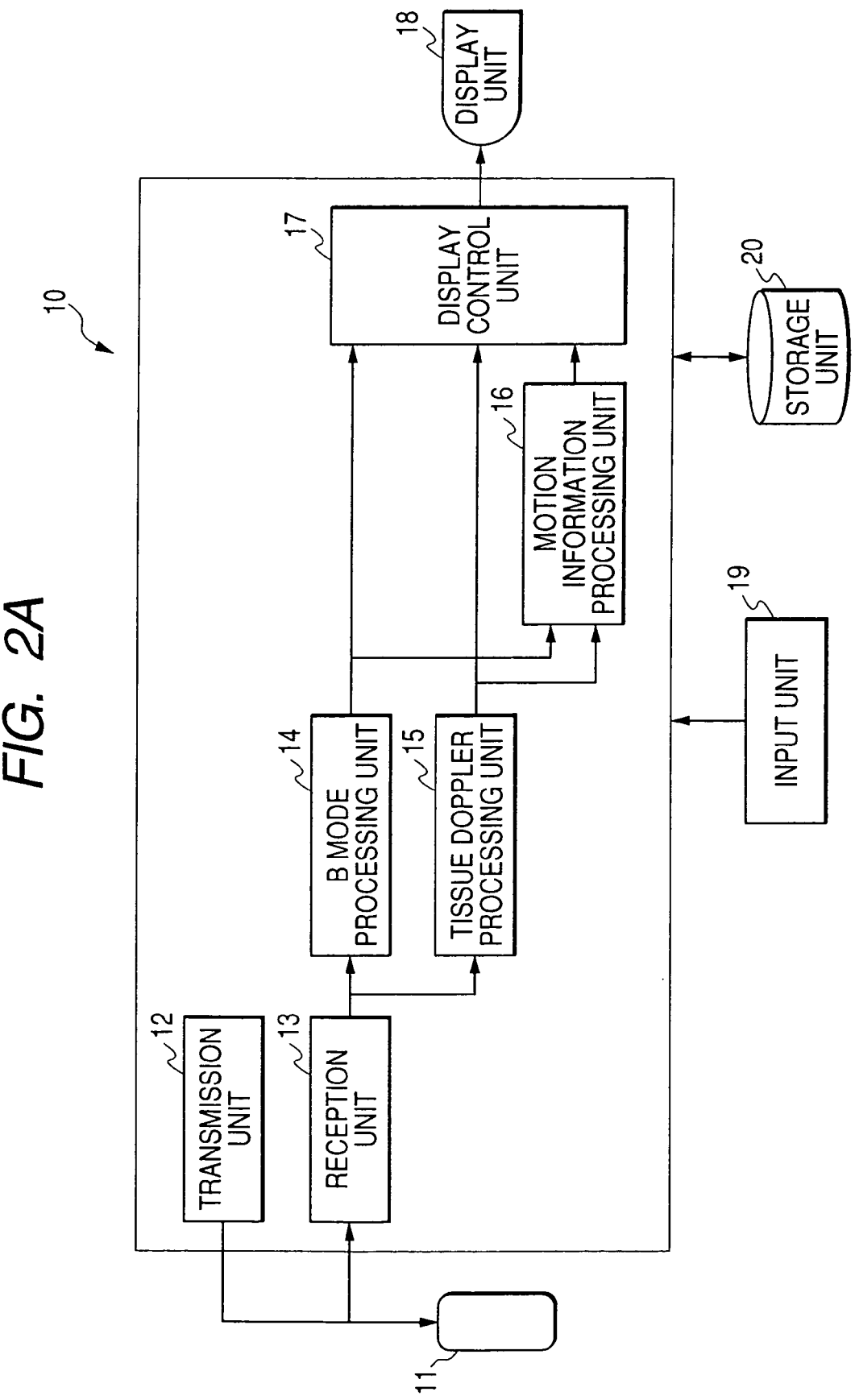
FIG. 2A is a block diagram illustrating a construction of an ultrasonic diagnostic instrument 10 according to a first embodiment.

FIG. 2A is a block diagram illustrating a structure of an ultrasonic diagnostic instrument 10 according to a first embodiment of the present invention. The ultrasonic diagnostic instrument 10 comprises an ultrasonic probe 11, a transmission unit 12, a reception unit 13, a B mode processing unit 14, a tissue Doppler processing unit 15, a motion information processing unit 16, a display control unit 17, a display unit 18, an input unit 19, and a storage unit 20.

The ultrasonic probe 11 comprises a plurality of piezoelectric vibrators for generating an ultrasonic wave in response to a driving signal from the transmission unit 12 and converting the reflected wave from a sample into an electrical signal, a matching layer provided in each piezoelectric vibrator, and a packing member for preventing the ultrasonic wave from propagating toward the rear side from each piezoelectric vibrator. When the ultrasonic wave is transmitted to the sample from the ultrasonic probe 11, various harmonic wave components are generated with propagation of the ultrasonic wave due to nonlinearity of a biological tissue. Basic wave components and harmonic wave components constituting the transmitted ultrasonic wave are rear-scattered due to the boundary of sound impedance of an internal tissue, minute scattering thereof, etc., and are received as the reflected wave (echo) by the ultrasonic probe 11. In this embodiment and respective embodiments to be described later, since a case where a heart is used as a radiography target is exemplified, the ultrasonic probe 11 is supposed as a sector probe.

The transmission unit 12 has a delay circuit, a pulser circuit, etc., which are not shown. The pulser circuit repeatedly generates a rate pulse for forming a transmission ultrasonic wave at a predetermined rate frequency fr Hz (period: 1/fr sec). In addition, the delay circuit concentrates the ultrasonic wave in a beam shape every channel and gives a delay time necessary for determining transmission directionality to the respective rate pulses. The transmission unit 12 applies a driving pulse to the respective vibrators to form an ultrasonic beam toward a predetermined scanning line at timings based on the rate pulses.

The reception unit 13 has an amplifier circuit, an A/D converter, an adder, etc., which are not shown. The amplifier circuit amplifies an echo signal received through the probe 11 every channel. The A/D converter gives a delay time necessary for determining reception directionality to the amplified echo signal and then the adder performs an addition process. Through this addition process, an ultrasonic echo signal corresponding to a predetermined scanning line is generated.

The B mode processing unit 14 generates a B mode signal corresponding to an amplitude intensity of the ultrasonic echo signal by performing an envelope wave detecting process to the ultrasonic echo signal received from the reception unit 13.

The tissue Doppler processing unit 15 performs an orthogonal wave detecting process, a self correlating process, etc. to the echo signal received from the reception unit 13, and obtains a tissue Doppler signal corresponding to the velocity, distribution, and power of a tissue which is being moved inside the sample on the basis of a Doppler shift component of the ultrasonic echo signal having been subjected to a delay and adding process.

The motion information processing unit 16 performs respective processes for acquiring motion information images such as a process of removing a translation velocity component and a rotation velocity component, etc. on the basis of the B mode signal and the Doppler signal output from the B mode processing unit 14 and the tissue Doppler processing unit 15. The function of estimating and removing the translation velocity component, etc. which is a specific operation of the motion information processing unit 16 will be described in detail later.

The display control unit 17 generates a B mode ultrasonic image indicating a two-dimensional distribution of the B mode signal in a predetermined cross section. The display control unit 17 also generates a tissue Doppler ultrasonic image indicating a two-dimensional distribution of the velocity, distribution, and power in a predetermined cross section on the basis of the tissue Doppler signal. The display control unit 17 also generates a superposed image of the B mode ultrasonic image and the tissue Doppler ultrasonic image, and a superposed image of the B mode ultrasonic image and a two-dimensional distribution image of displacement or distortion as needed.

The display unit 18 displays morphological information or blood flow information inside the biological body as an image on the basis of a video signal from the display control unit 17. When a contrast agent is used, the display unit also displays a gray-scale image or a color image on the basis of a spatial distribution of the contrast agent, that is, quantitative information amount of an area where the blood flow or blood exists.

The input unit 19 is connected to an instrument body and has a mouse or a track ball, a mode conversion switch, a keyboard, etc. for receiving various instructions from an operator such as an instruction of setting a region of interest (ROI), an instruction of setting various image quality conditions, etc. into the instrument body.

The storage unit 20 stores the ultrasonic image data (ultrasonic data) corresponding to the respective time phases, velocity distribution image corresponding to the respective time phases and generated by the motion information processing unit 16, etc. The ultrasonic image data includes the tissue image data radiographed in the tissue Doppler mode and the tissue image data radiographed in a mode other than the tissue Doppler mode. In addition, the tissue image data may include so-called raw image data before scan conversion.

(Tissue Tracking Imaging)

Next, the tissue tracking imaging method that is a premise technique of this embodiment will be described in brief. Details of this technique are disclosed in, for example, Japanese Patent Application No. 2002-272845. A spatiotemporal distribution image of a tissue velocity is required for the tissue tracking imaging method. The spatiotemporal distribution image of a tissue velocity (hereinafter, referred to as "velocity distribution image") is generated from the ultrasonic image data of a plurality of time phases collected through the tissue Doppler method or is obtained by performing a pattern matching process to a plurality of two-dimensional tissue images of a plurality of time phases collected in the B mode. In this embodiment, the velocity distribution image generated through the former method is utilized. The latter method will be described in a second embodiment.

Figure 2B:
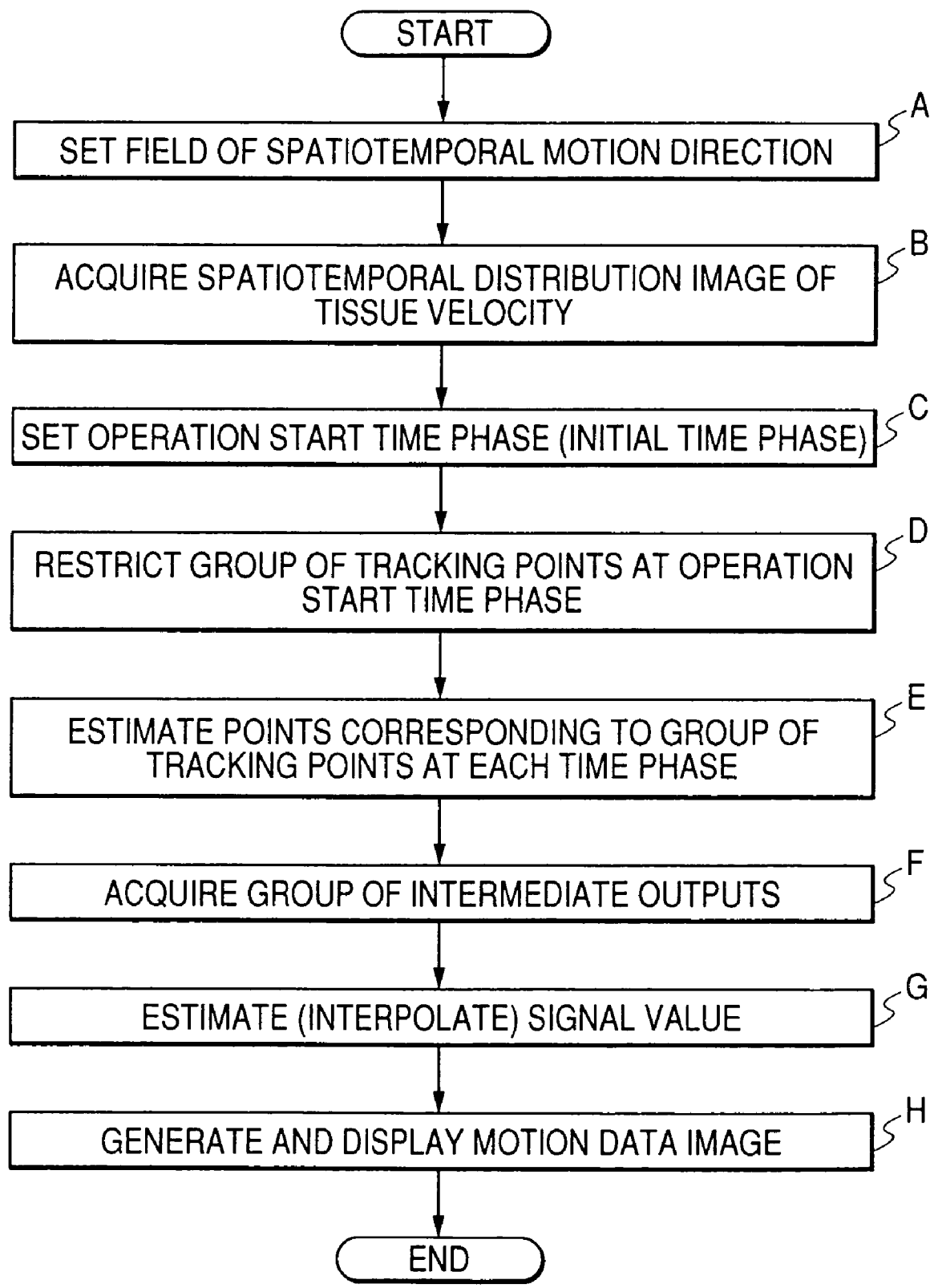
FIG. 2B is a flowchart illustrating a flow of processes in observing a heart using a tissue tracking imaging (TTI) method according to the first embodiment.

FIG. 2B is a flowchart illustrating a flow of processes in observing a heart by using the tissue tracking imaging method according to the present embodiment. As shown in FIG. 2B, first, a motion field of a spatiotemporal motion direction is set on an image plane (step A). That is, as a motion field for the tissue tracking to be performed in future, for example, any one of a contraction motion field having a motion direction being radial about the contraction center of heart and a rotation motion field having a motion direction being angular about the contraction center of a heart is selected and set (here, it is supposed that the contraction motion field is set). A motion field is a field (vector field) in which a motion direction is defined at each point. Therefore, the motion direction at each point is set by setting the motion field.

Next, a velocity distribution image of a mobile portion in a sample is obtained at each time phase on the basis of the ultrasonic image data of a plurality of time phases collected through the tissue Doppler method, and information of the motion field in which the motion direction of a tissue is defined is stored (step B).

Next, a group of tracking points at an operation start time phase is set finitely (step D). The temporal movement of the group of tracking points is tracked on the basis of the velocity distribution image, and corresponding points corresponding to the respective tracking points at each time phase are estimated (step E).

Next, predetermined intermediate output values such as displacement, distortion, etc. are calculated based on the group of tracking points and estimated corresponding points (step F), and a signal value for imaging is estimated at each point on the basis of the intermediate output values (step G). Finally, the motion information image comprising the signal values is generated and displayed on a monitor (step H).

(Function of Calculating and Removing Translation Velocity Component)

Next, a function of calculating and removing a translation velocity component in the ultrasonic diagnostic instrument 10 will be described. This function is performed in a process (that is, step B of FIG. 2B) of acquiring a spatiotemporal velocity distribution image in the tissue tracking imaging method. For the purpose of specific description, a minor axis model of a heart is exemplified as a target.

First, the minor axis model that is supposed in this embodiment will be described. In the minor axis model, it is supposed that "the translation velocity component of each position is equal to a movement velocity of the contraction center". For example, as disclosed in "Applicability of Center Line Technique Applied to Sectional Center Echo Diagram Method", Ishii et al, Hikosy's collection of works on medical theories 56: P157-158, 1990, this hypothesis is based on that the translation velocity component of each position in a heart depends upon the translation motion of "the whole heart" and thus the translation velocity components of the respective points in a left ventricle are substantially equal to each other if the time phases thereof are equal to each other.

Figure 3:
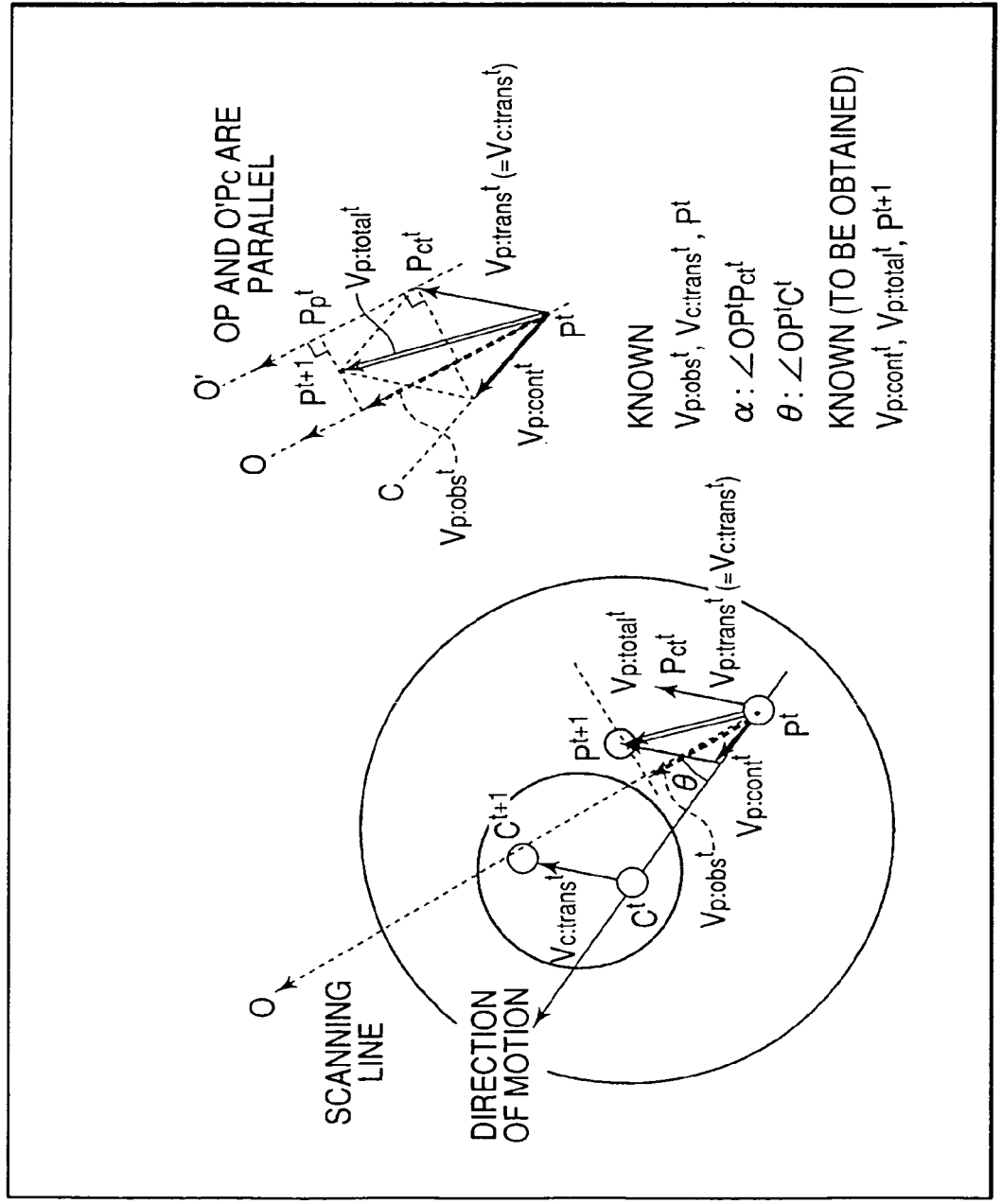
FIG. 3 is a diagram illustrating a minor axis model under assumption.

FIG. 3 is a diagram illustrating a minor axis model which is supposed. Symbols shown in FIG. 3 and the flowing description denote the following details (where an observation system is located on a ground).

$P^t$: position of a point P at a time phase t $C^t$: position of a contraction center C at a time phase t $V_{p:total}^t$: velocity of a tissue at a point $P^t$ $V_{p:cont}^t$: contraction (expansion) velocity component of a tissue at a point $P^t$ $V_{c:trans}^t$: translation velocity component at a point $C^t$ $V_{p:trans}^t$: translation velocity component of a tissue at a point $P^t$ $V_{p:rot}^t$: rotation velocity component of a tissue at a point $P^t$ (where, $V_{p:rot}^t = 0$ is supposed in FIG. 3)

At a time point t (in this case, a time phase t), motion components which should be considered at a position of a predetermined point $P^t$ of a cardiac muscle include an expansion and contraction component $V_{p:cont}^t$, a translation velocity component $V_{p:trans}^t$, and a rotation velocity component $V_{p:rot}^t$ of a local cardiac muscle. That is, the velocity obtained by synthesizing the three velocity components is generated on the point $P^t$ as a tissue velocity $V_{p:total}^t$ at the point $P^t$.

$$V_{p:total}^t = V_{p:cont}^t + V_{p:trans}^t + V_{p:rot}^t \tag{1}$$

where $V_{p:total}^t$, $V_{p:cont}^t$, $V_{p:trans}^t$, and $V_{p:rot}^t$ are all vector velocities. Now, for the purpose of simplification, a model where the rotation component is neglected by $V_{p:rot}^t = 0$ and the velocity $V_{p:obs}^t$ at the point P is observed at the time phase t using the tissue Doppler method will be described.

First, since $V_{p:rot}^t = 0$ in the above equation, the equation (1) can be expressed as the following equation (2).

$$V_{p:total}^t = V_{p:cont}^t + V_{p:trans}^t \tag{2}$$

In this model, it is considered that the unknown information $V_{p:cont}^t$, $V_{p:total}^t$, and $P^{t+1}$ are obtained from the known information of $V_{p:obs}^t$, $V_{p:trans}^t$, $P^t$, $\alpha = \angle OP^t P_{ct}^t$, and $\theta = \angle OP^t C^t$. $P_{ct}^t$ means a point obtained by moving in parallel $P^t$ by $V_{p:trans}^t$ (that is, a point for $P^t$ to be moved through the translation motion).

By setting an angle formed between the scanning line and the motion direction of the point $P^t$ as $\theta$, the following equations (3) and (4) can be obtained from the right-upper diagram of FIG. 3.

$$|P_p^t - P_{ct}^t| = |V_{p:cont}^t| \cdot \cos\theta \qquad (3)$$

$$|V_{p:obs}^t| = |P_p^t - P_{ct}^t| + |V_{p:trans}^t| \cdot \cos\alpha \qquad (4)$$

Accordingly, $V_{p:cont}^t$ can be obtained from the following equation (5).

$$|V_{p:cont}^t| = (|V_{p:obs}^t| - |V_{p:trans}^t| \cdot \cos\alpha)/\cos\theta \qquad (5)$$

The direction ($C^t - P^t$) of $V_{p:cont}^t$ can be obtained using a predetermined method. Therefore, the vector velocity of $V_{p:cont}^t$ can be obtained from the equation (5).

$V_{p:total}^t$ can be obtained from $V_{p:cont}^t$ and $V_{p:trans}^t$ calculated by the following equation (6) by setting dt=(time phase t+1)−(time phase t).

$$V_{p:trans}^t = (C^{t+1} - C^t)/dt \qquad (6)$$

Although it has been omitted in this embodiment, the corresponding point $P^{t+1}$ at a time phase next to the point $P^t$ can be estimated by $P^{t+1} = P^t + V_{p:total}^t \cdot dt$ in accordance with the tissue tracking imaging method.

It should be noted that an accurate result cannot be obtained at a region where $\cos\theta$ is close to 90 degree in the equation (5). Therefore, it is preferable that a Doppler limit area be set within such a range. Specific details thereof will be described in a third embodiment.

Figure 4:
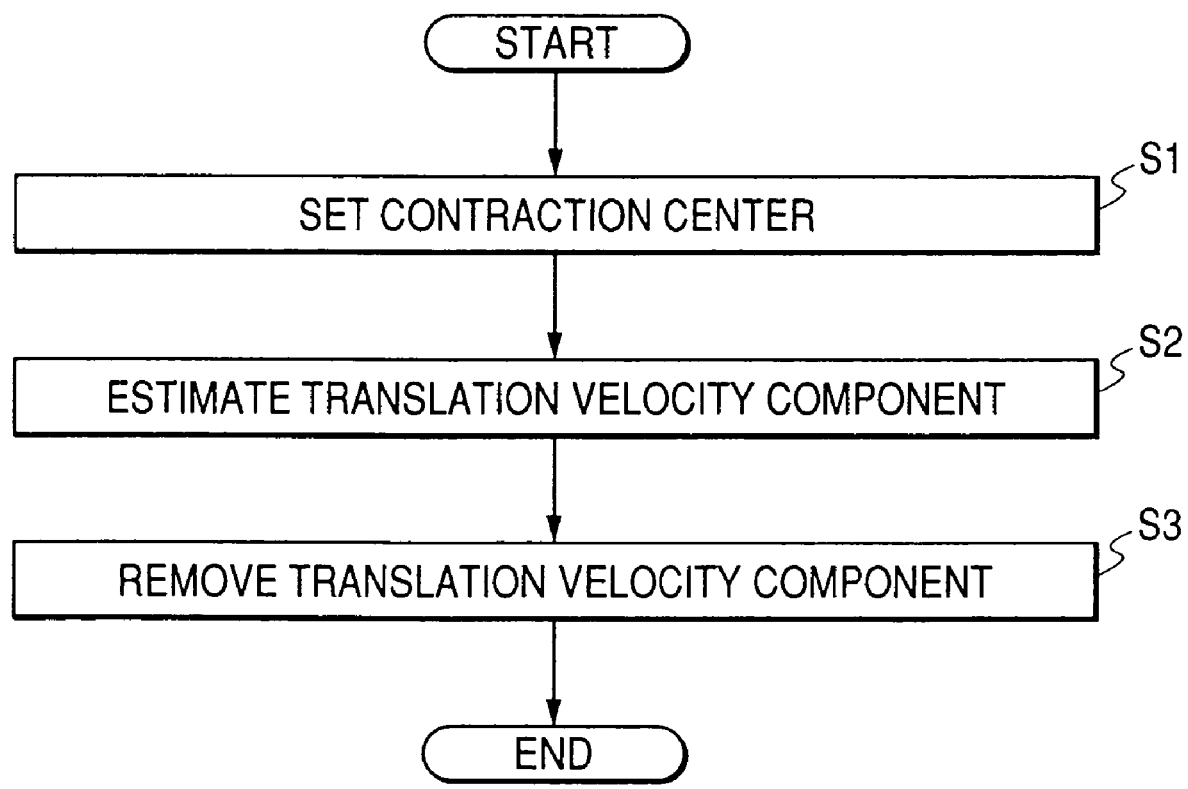
FIG. 4 is a flowchart illustrating a flow of processes to be performed in a function of calculating and removing a translation velocity component.

Next, the function of calculating and removing a translation velocity component in the above-mentioned model will be described specifically. FIG. 4 is a flowchart illustrating a flow of processes to be performed in the function of calculating and removing the translation velocity component. As shown in FIG. 4, the flowchart comprises three processes of a process of setting a contraction center, a process of estimating a translation velocity component, and a process of removing a translation velocity component.

<Setting Contraction Center: Step S1>

The process of setting a contraction center can be embodied, for example, using several methods disclosed in Japanese Patent Application No. 2002-272845. However, a function of semi-automatically setting a contraction center in the ultrasonic diagnostic instrument 10 will be described. In this semi-automatic setting function, a position at a time phase of which the positioning is omitted is estimated from the positions at the time phases set before and after the time phase using a linear interpolation process. As for the linear interpolation, in the images associated with both time phase of the initial time and the final time (the initial time phase and the final time phase) having only one end, a temporal automatic ending process is performed to save a labor of positioning by a user as much as possible.

Figure 5:
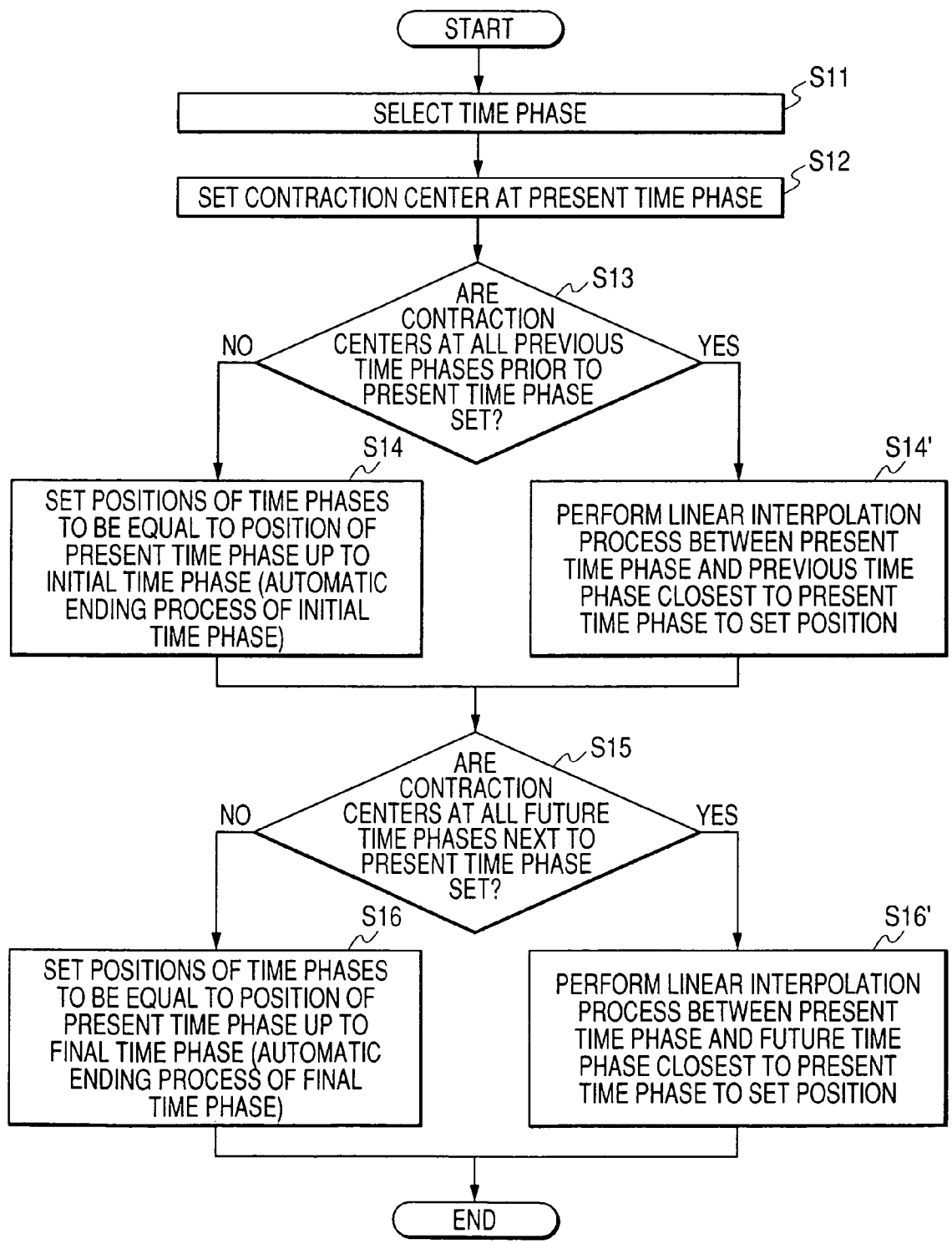
FIG. 5 is a flowchart illustrating an algorithm of a semi-automatic setting function.
Figure 6:
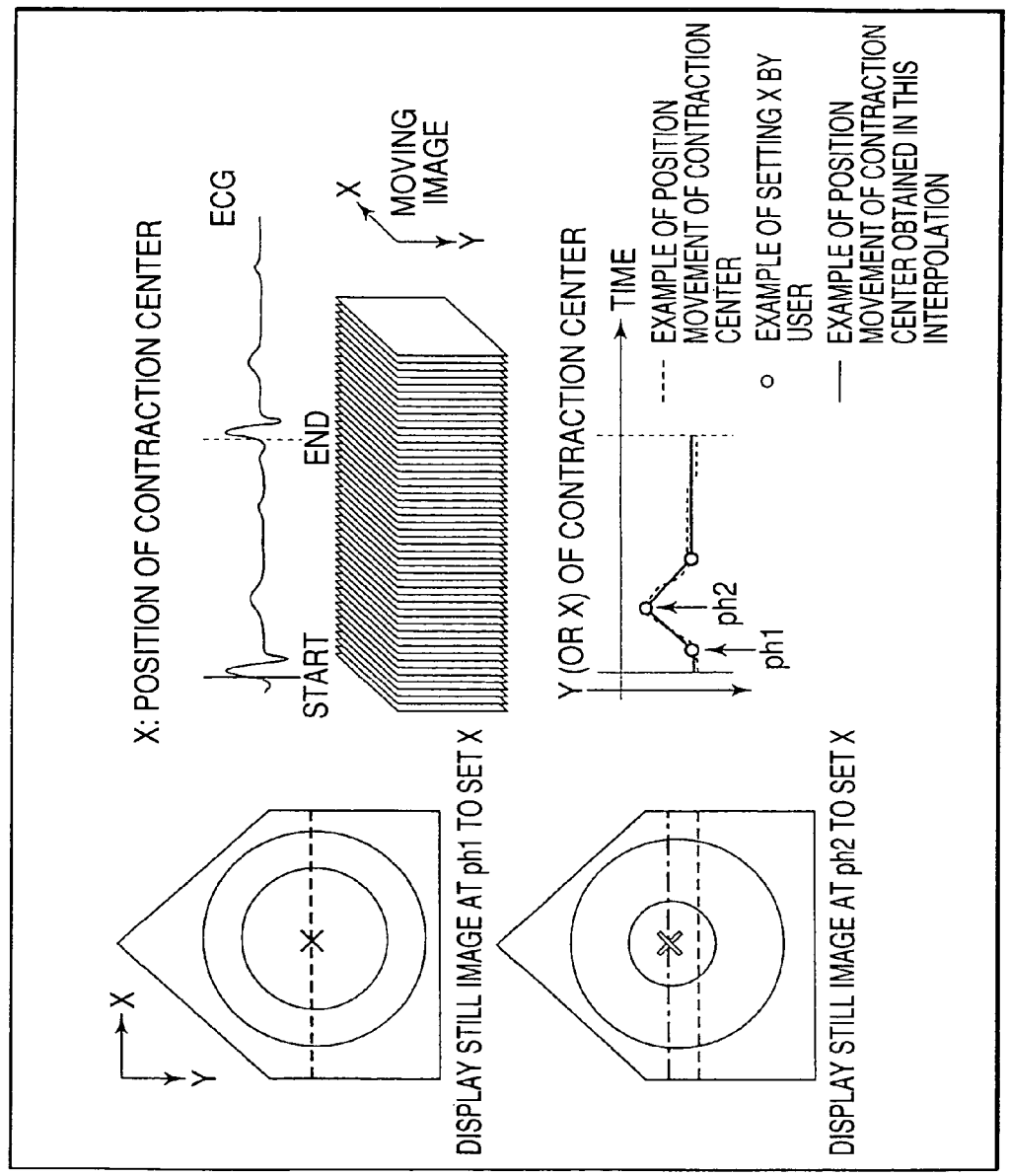
FIG. 6 is a conceptual diagram illustrating the semi-automatic setting function.

FIG. 5 is a flowchart illustrating an algorithm for the semi-automatic setting function. FIG. 6 is a conceptual diagram illustrating the semi-automatic setting function.

As shown in FIG. 5, first, an image at a predetermined time phase is selected (step S11), and then a contraction center is positioned (step S12). Next, it is checked whether the positioning is completed at a previous time phase before the present time phase having been positioned (step S13), and when the positioning is not completed at the previous time phase, the positions of the time phases up to the initial time phase are set to the position of the present time phase (automatic ending process of the initial time phase: step S14). On the other hand, when the positioning is completed at the previous time phase, the positioning is performed between the present time phase and a previous time phase closest to the present time phase using the linear interpolation process (step S14').

Next, it is checked whether the positioning is completed at a future time phase after the present time phase having been positioned (step S15), and when the positioning is not completed at the future time phase, the positions of the time phases up to the final time phase are set to the position of the present time phase (automatic ending process of the final time phase: step S16). On the other hand, when the positioning is completed at the future time phase, the positioning is performed between the present time phase and a future time phase closest to the present time phase using the linear interpolation process (step S16').

The analysis of data on a heart is generally performed in a unit of cardiac cycle and it may thus take a labor for an operator to set a contraction center. However, according to the above algorithm, since the position (X) of the contraction center at the initial time phase (start) and the final time phase (end) is constant when one cardiac cycle is set as an analysis target, the positioning at two time phases of the initial time phase and the final time phase can be omitted.

Therefore, a user can simply perform the positioning of the contraction center in one cardiac cycle with practical accuracy through the positioning of at least two time phases to three time phases as schematically shown in FIG. 6 (preferably, ph1 is an R wave time phase of end diastole and ph2 is a end systole time phase).

When the automatic ending process is not performed, it is possible to set the position of the contraction center in an image corresponding to the overall time phase as a processing target by positioning four time phases to five time phases including both ends.

In addition to the semi-automatic setting function, for examples, in a trace surface of an endocardium obtained by the automatic profile extracting technique disclosed in "Ultrasonic method of extracting a dynamic profile of a heart wall with a partial-shape restriction profile model", Institute of Electronics, Information and Communication Engineers, D-II Vol. J83-D-II No. 1, pp. 183-190 (January 2000), the contraction center is set to the center of gravity of the surface. According to this technique, the contraction center can be set automatically and dynamically in accordance with the shape or the motion data of the endocardium.

<Estimating Translation Velocity Component>

Next, details of the process of estimating the translation velocity component $V_{p:trans}^t$ will be described. In this estimation process, the translation velocity component at the present time phase is estimated as follows, on the assumption that "the translation velocity component at each position is equal to the movement velocity of the contraction center (that is, $V_{p:trans}^t = V_{c:trans}^t$)".

Figure 7:
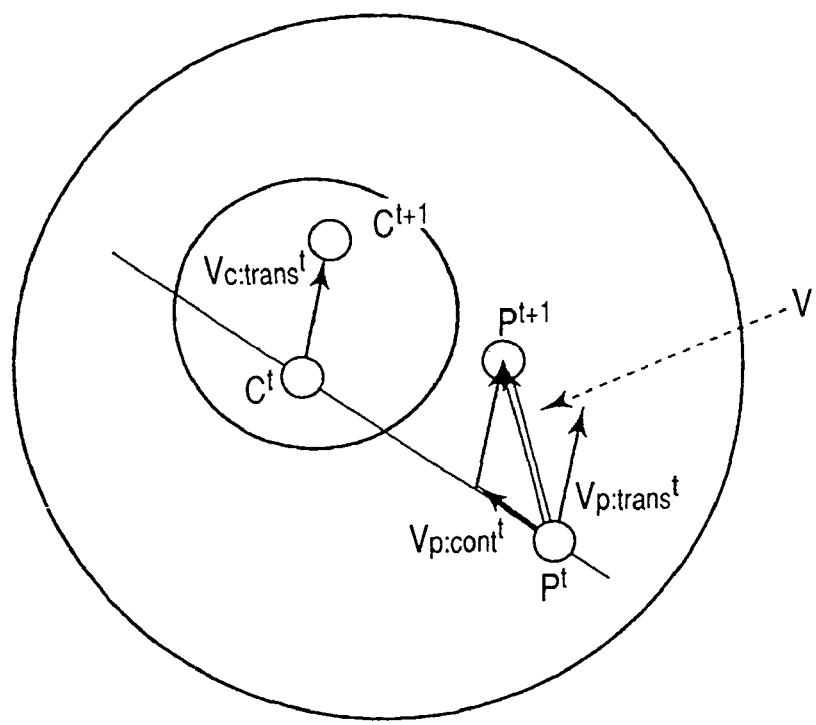
FIG. 7 is a diagram illustrating a process of estimating a translation velocity component.

That is, for example, as shown in FIG. 7, when the contraction center $C^t$ is moved to $C^{t+1}$ with the translation motion, the translation velocity component $V_{p:trans}^t$ can be obtained from the equation (6) of $V_{p:trans}^t = (C^{t+1} - C^t)/dt$ by setting dt= (time phase t+1)−(time phase t). Since $C^t$ and $C^{t+1}$ are two-dimensional coordinates, $V_{p:trans}^t$ is a vector velocity.

Here, using the contraction center as an object in the equation (6), as the simplest example, the present velocity is estimated from variation of the present position to the future position. However, this embodiment is not limited to the example, but the present velocity may be estimated from variation of the previous position to the present position and the present velocity may be estimated from variation in position at a plurality of previous or future time phases including the present time phase. However, in any case, at end portions of the defined analysis time period (initial and final time phase), an ending process is required using external data when data exists outside of the definition or using only the present velocity and velocities of available time phases adjacent the present velocity when data do not exist outside the definition.

<Removing Translation Velocity Component>

Next, the process of removing the translation velocity component $V_{p:trans}^t$ will be described. On the above assumption, the same component as $V_{p:trans}^t$ defined at the contraction center is also generated at the point P'. Therefore, for the purpose of simplification, supposed that the rotation velocity component is $V_{p:rot}^t=0$, the velocity vector component of the point P' becomes $V_{p:total}^t$ obtained by synthesizing the contraction velocity component $V_{p:cont}^t$ in the motion direction and the translation velocity component $V_{p:trans}^t$ (see Equation (1)). Therefore, $V_{p:cont}^t$ can be obtained by the following equation (7) transformed from the equation (2).

$$V_{p:cont}^t = V_{p:total}^t - V_{p:trans}^t \qquad (7)$$

where $V_{p:total}^t$, $V_{p:cont}^t$, and $V_{p:trans}^t$ are all vector velocities. In this way, the velocity component $V_{p:cont}^t$ in the motion direction (the contraction and expansion direction) to be originally detected, which the translation velocity component has been removed from, is obtained (for example, where the direction toward the contraction center is a positive direction and the direction apart from the contraction center is a negative direction) and is converted into a scalar defined by $|V_{p:cont}^t|$.

If imaging $|V_{p:cont}^t|$ obtained in this process, it is possible to image the contraction and expansion velocity from which the translation velocity component is removed.

<Application to Tissue Tracking Imaging>

Next, application to the tissue tracking imaging method will be described. In the tissue tracking imaging method, first, it is necessary to track a point P. A velocity vector used in this tracking is $V_{p:total}^t$, that is, the velocity vector itself of the point P at the time phase t. In this regard, $V_{p:total}^t$ is equivalent to a synthesized vector of the velocity component in the motion direction to be originally detected and the translation velocity component. The position $P'^{t+1}$ of the point P at the time phase t+1 is tracked from the following equation (8) using $V_{p:total}^t$.

$$P'^{t+1} = P'^t + V_{p:total}^t \cdot dt \qquad (8)$$

where $V_{p:total}^t \cdot dt$ is a displacement vector amount.

Next, it is necessary to define an intermediate value of the motion information at the tracked position, but it is preferable that the component $|V_{p:cont}^t|$ of each tracking point at each time phase be used as the velocity component used for defining the intermediate value unlike the case of the tracking. The intermediate value of the vector at each time phase is obtained by integrating the component $|V_{p:cont}^t|$ with time while tracking the position, and when this intermediate value is converted into the final output, by taking the absolute value of the vector (when the direction toward the contraction center is a positive direction and the direction apart from the contraction center is a negative direction) to convert the vector into a scalar, it is possible to image the distortion or displacement using the motion information in the expansion and contraction direction from which the translation velocity component or the rotation velocity component is removed. The imaging of the motion information is described, for example, in Japanese Patent Application No. 2002-272845 described above.

By removing the translation velocity component through a series of processes described above, it is possible to obtain an output image display of a characteristic quantity of the tissue motion in the supposed motion direction from which an error is reduced.

According to this ultrasonic diagnostic instrument, since the motion information image can be generated using the information from which the translation velocity component due to movement of a body, etc. is removed, it is possible to provide a diagnostic image having higher reliability.

According to the ultrasonic diagnostic instrument, it is possible to set a contraction center of a heart at a predetermined time phase using the linear interpolation process with information about the time phases before and after the predetermined time phase and it is also possible to automatically set a contraction center of a heart at the initial time phase and the final time phase using the semi-automatic setting function. Therefore, it is possible to reduce a work burden of an operator and to enhance work efficiency.

Second Embodiment

Next, a second embodiment of the present invention will be described. The second embodiment utilizes velocity distribution images generated by performing the pattern matching process to a plurality of two-dimensional tissue images at a plurality of time phases collected in the B mode, etc.

Figure 8:
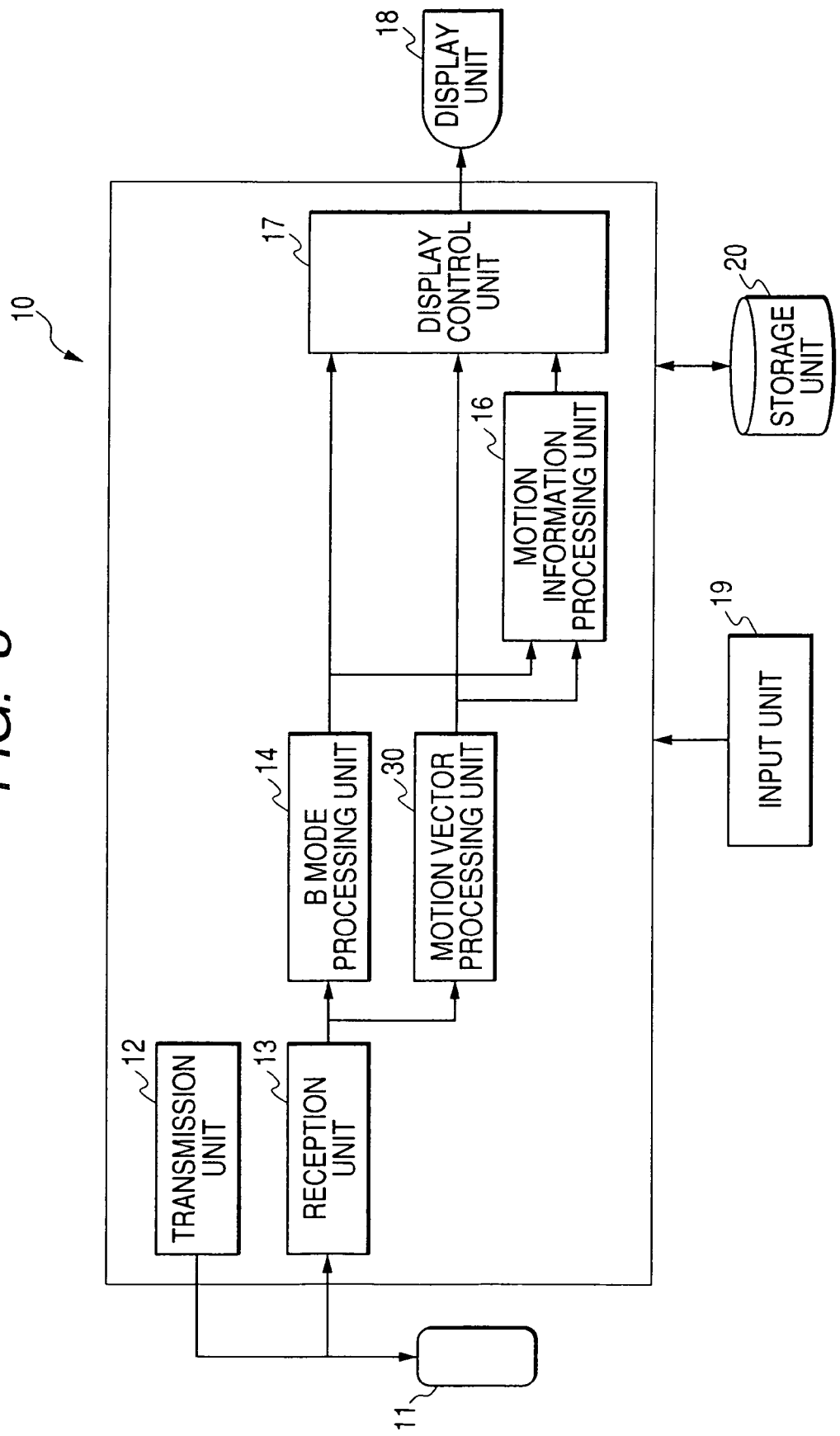
FIG. 8 is a block diagram illustrating a construction of an ultrasonic diagnostic instrument 10 according to a second embodiment.

FIG. 8 is a block diagram illustrating a construction of an ultrasonic diagnostic instrument 10 according to this embodiment. FIG. 8 is substantially equal to FIG. 2A, except that the tissue Doppler processing unit 15 is replaced with a motion vector processing unit 30.

The motion vector processing unit 30 detects a moved position of a tissue between two ultrasonic tissue images (for example, B mode images) having different time phases using the pattern matching process, and calculates a tissue velocity on the basis of the moved position. Specifically, the motion vector processing unit extracts a partial image from a first ultrasonic image and obtains a position having highest similarity to the partial image in a second ultrasonic image. The motion vector processing unit can obtain the motion velocity of the tissue by calculating a distance between the position in the second ultrasonic image and the position of the partial image in the first ultrasonic image and dividing the distance by a time difference between the first ultrasonic image and the second ultrasonic image. By performing this process to the respective points of the ultrasonic image, it is possible to obtain the velocity distribution image of the tissue movement.

The motion information processing unit 16 obtains the two-dimensional distribution image (motion information image) of the displacement or distortion in a predetermined cross section on the basis of the velocity distribution image output from the motion vector processing unit 30.

Figure 9:
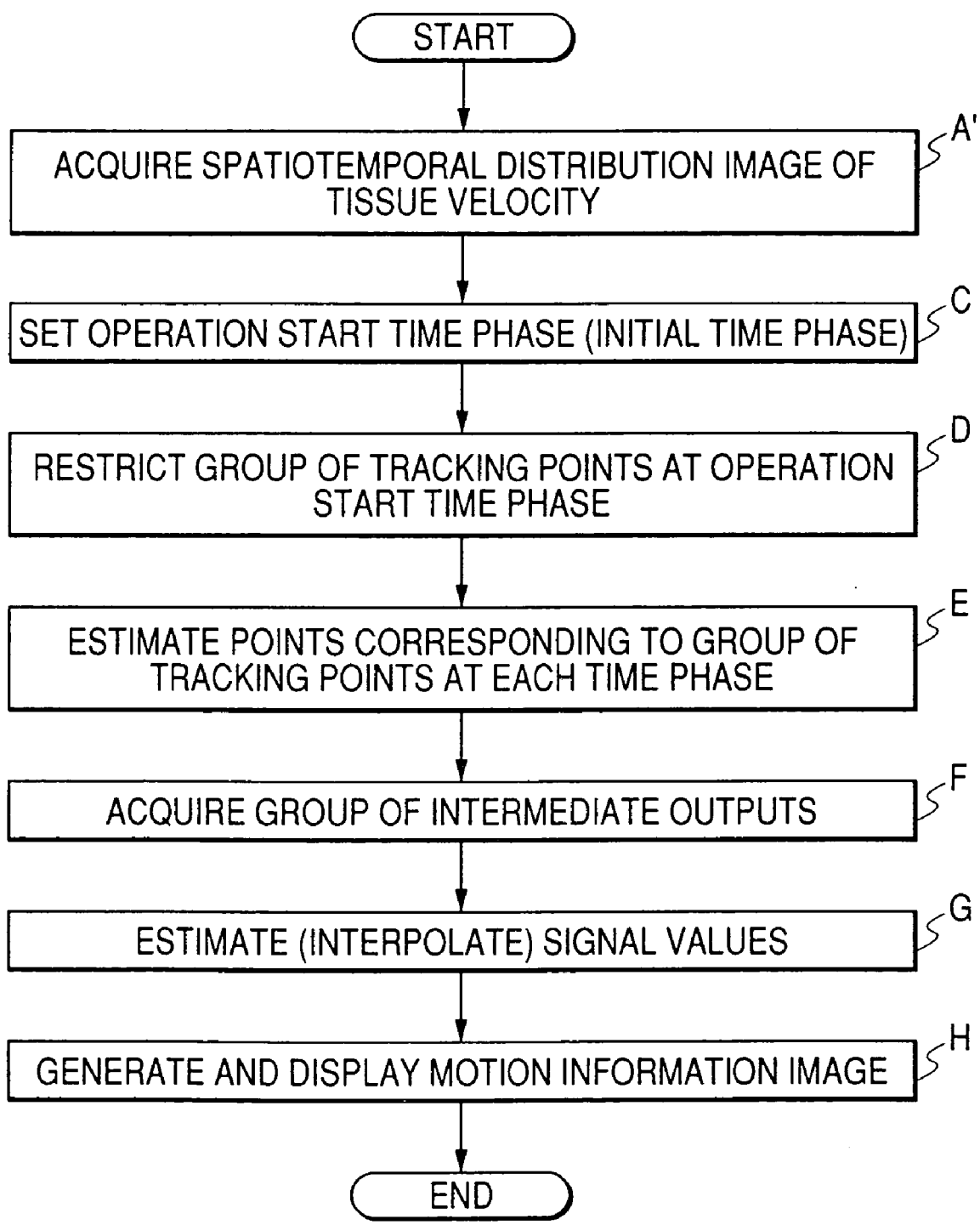
FIG. 9 is a flowchart illustrating a flow of processes in observing a heart using the tissue tracking imaging (TTI) method according to the second embodiment.

FIG. 9 is a flowchart illustrating a flow of processes in observing a heart using the tissue tracking imaging method according to this embodiment. The process of the tissue tracking imaging method is substantially equal to the series of processes shown in FIG. 2B, except for the step A'. At the step A', the velocity distribution image of the tissue movement is acquired by the motion vector processing unit 30.

(Function of Calculating and Removing Translation Velocity Component)

Next, the function of calculating and removing the translation velocity component of the ultrasonic diagnostic instrument 10 will be described. The function of calculating and removing the translation velocity component is also simultaneously performed in the process (that is, the step A' of FIG. 9) of acquiring the spatiotemporal velocity distribution image of the tissue tracking imaging method, and uses the minor axis model of a heart as a target. Now, the respective processes performed in the function of calculating and removing the translation velocity component will be described with reference to FIG. 4.

<Setting Contraction Center: Step S1>

First, a process of setting a contraction center will be described. The process of setting a motion field is not necessary in principle for tracking a point using the velocity distribution image with the pattern matching process as in this embodiment. However, considering the object of this embodiment of calculating a velocity component in a predetermined motion direction, it is supposed that a field of a predetermined motion direction is set. Here, by supposing that the thickening direction is detected in a cross section of a minor axis, the process of setting a contraction center is performed.

It is preferable that the semi-automatic setting function (that is, the two-point linear interpolation process and the ending process) described above be used as a specific method of setting a contraction center. As another example of a method of setting a contraction center, the automatic profile extracting technique described above may be used.

<Estimating Translation Velocity Component>

The process of estimating a translation velocity component $V_{p:trans}^t$ is similar to the corresponding process of the first embodiment.

<Removing Translation Velocity Component>

The process of removing a translation velocity component $V_{p:trans}^t$ is also similar to the corresponding process of the first embodiment. If the rotation velocity component of the contraction center $V_{c:trans}^t$ is obtained, an angle β formed between $V_{c:trans}^t$ and the motion direction to be detected, that is, the contraction and expansion direction is obtained.

<Application to Tissue Tracking Imaging>

Next, the application to the tissue tracking imaging will be described. In the tissue tracking imaging, first, it is necessary to track a point P.

As the velocity component used for defining an intermediate value, it is preferably that the component $|V_{p:cont}^t|$ of the respective tracking points at each time phase be used unlike the case of tracking. The intermediate value of the vector at each time phase is obtained by integrating the component $|V_{p:cont}^t|$ with time while tracking the position, and when this intermediate value is converted into the final output, by taking the absolute value of the vector (when the direction toward the contraction center is a positive direction and the direction apart from the contraction center is a negative direction) to convert the absolute value of the vector into a scalar, it is possible to image the distortion or displacement using the motion information in the expansion and contraction direction from which the translation velocity component or the rotation velocity component is removed. The imaging of the motion information is described, for example, in Japanese Patent Application No. 2002-272845 described above.

(Function of Calculating and Removing Rotation Velocity Component)

Next, a function of calculating and removing a rotation velocity component of the ultrasonic diagnostic instrument 10 will be described. This function can be embodied on the assumption that "the rotation velocity component $V_{c:trans}^t$ is perpendicular to the contraction velocity component $V_{p:cont}^t$" in the minor axis model.

Figure 10:
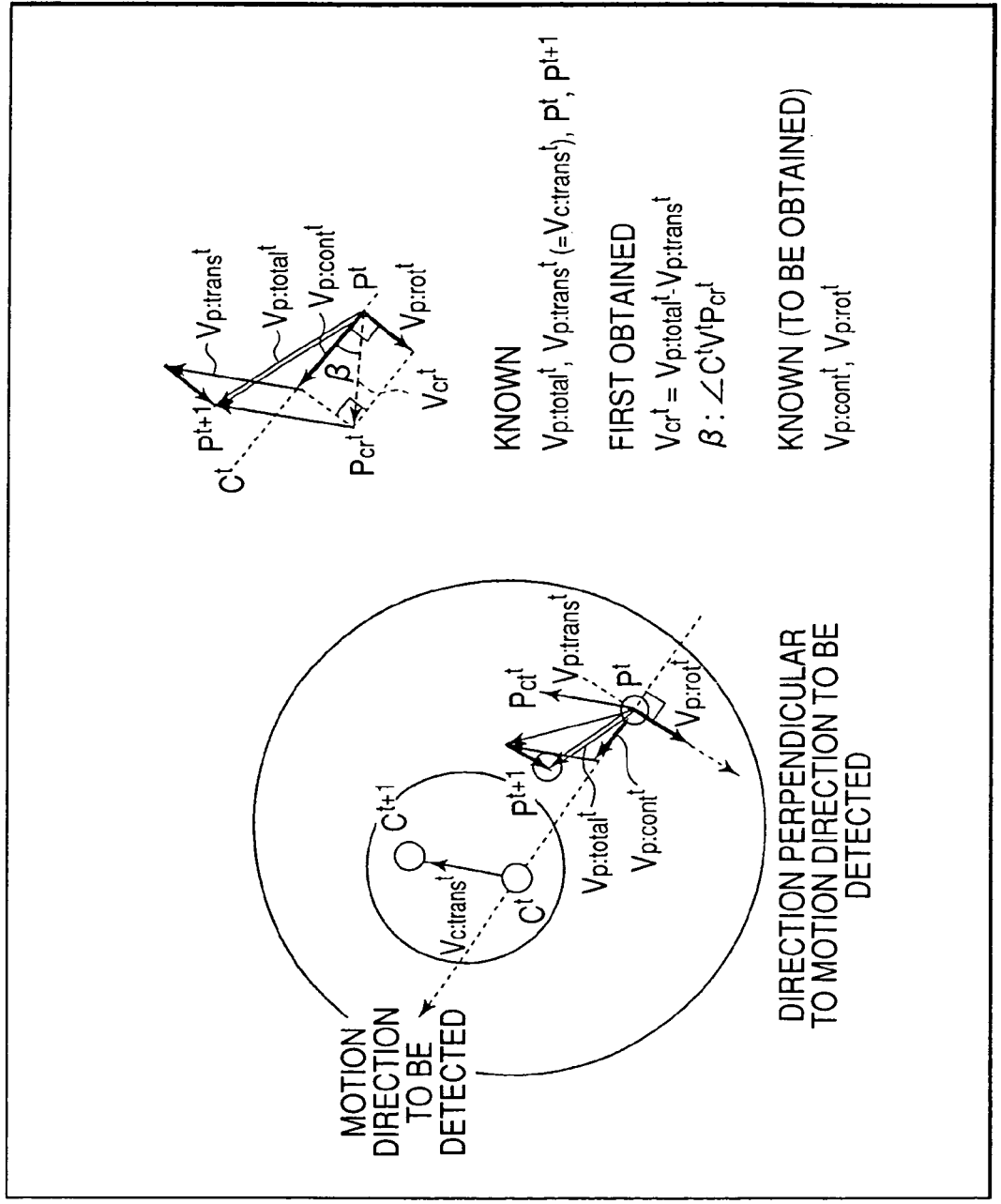
FIG. 10 is a conceptual diagram illustrating a function of calculating and removing a rotation velocity component.

FIG. 10 is a conceptual diagram illustrating the function of calculating and removing a rotation velocity component. As can be seen from the right side of FIG. 10, $V_{p:cont}^t$ and $V_{p:rot}^t$ can be obtained from the following equations.

$$V_{p:cont}^t = V_{C:rot}^t \cdot \cos \beta \tag{9}$$

$$V_{p:cont}^t = V_{C:rot}^t \cdot \sin \beta \tag{10}$$

where $V_{C:rot}^t$ is a rotation velocity component of the contraction center $C^t$ at a time phase t. The estimation operation according to the above equations may be performed at the step S2 of FIG. 4 and the removal operation may be performed at the step S3 of the same figure.

In this way, the velocity component $V_{p:cont}^t$ in the motion direction to be originally detected, which the translation velocity component and the rotation velocity component have been all removed from, is obtained (for example, where the direction toward the contraction center is a positive direction and the direction apart from the contraction center is a negative direction) and is converted into a scalar defined by $|V_{p:cont}^t|$. If $|V_{p:cont}^t|$ is imaged in this step, it is possible to image the contraction and expansion velocity from which the contraction velocity component and the rotation velocity component have been all removed.

In a case in which the motion direction to be detected is supposed as the rotation component (in a rotation motion field), it is possible to obtain the rotation motion information (velocity, distortion, and displacement) from which the translation component due to the whole movement of a heart and the contraction component have been removed, by using the component $V_{p:rot}^t$ as velocity information (of which the detailed steps are omitted). In this case, it is preferable that for example, the clockwise direction be defined as a positive direction and the counterclockwise direction be defined as a negative direction when the vector is converted into the final output.

Third Embodiment

Next, a third embodiment will be described. In the third embodiment, more effective motion information images are generated, by using both the velocity distribution image generated from the ultrasonic image data at a plurality of time phases collected through the tissue Doppler method and the velocity distribution image obtained by performing the pattern matching process to a plurality of two-dimensional tissue images at a plurality of time phases collected through the B mode method, etc.

Figure 11:
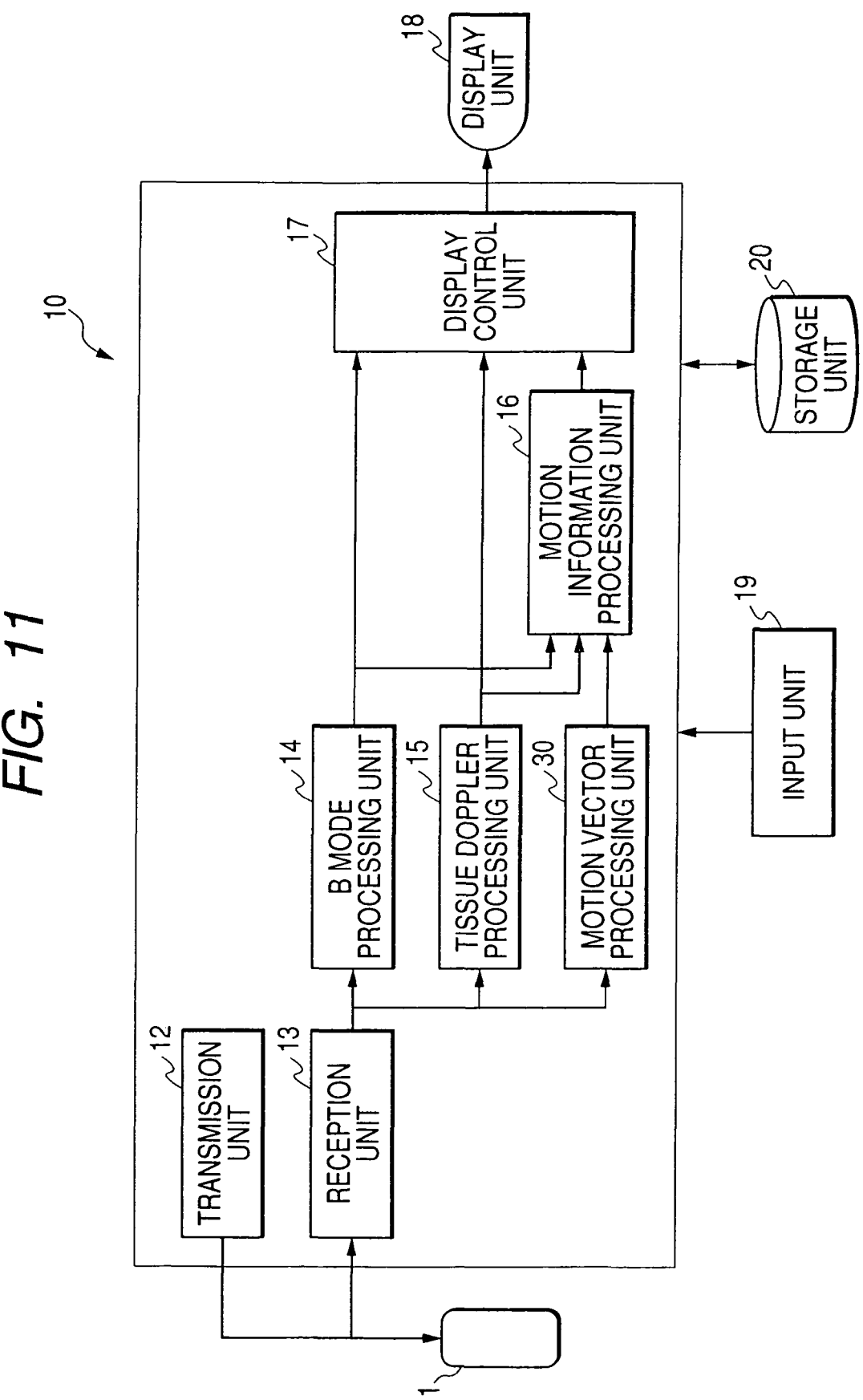
FIG. 11 is a block diagram illustrating a construction of an ultrasonic diagnostic instrument 10 according to a third embodiment.

FIG. 11 is a block diagram illustrating a construction of the ultrasonic diagnostic instrument 10 according to this embodiment. In FIG. 11, the ultrasonic diagnostic instrument comprises both the tissue Doppler processing unit 15 and the motion vector processing unit 30.

The motion information processing unit 16 generates the motion information image in accordance with a synthesis function of the tissue Doppler method and the pattern matching method (hereinafter, simply referred to as "synthesis function") to be described later, using the method according to the first embodiment outside a Doppler angle-correction limit area (an area where the Doppler angle-correction is not valid) and using the method according to the second embodiment inside the Doppler angle-correction limit area, respectively, and generates a synthesis image obtained by synthesizing both motion information images and displays the synthesis image in the display unit 18.

In addition, the motion information processing unit 16 performs a display control that the contraction centers are matched for display when the plurality of motion information displays the images in time series.

The display unit 18 displays the synthesis image to be described below and performs a predetermined display in accordance with a display function to be described later.

(Synthesis Function)

Next, the synthesis function according to this embodiment will be described. The synthesis function includes three processes of a process of generating a velocity distribution image inside and outside the Doppler angle-correction limit area, a process of correcting an angle of a velocity inside the Doppler angle-correction limit area, and a process of synthesizing images.

<Generating a Velocity Distribution Image Inside and Outside the Doppler Angle-Correction Limit Area>

The respective motion information images according to the first and second embodiments described above are generated, and the velocity information images are properly used depending upon the inside or outside of the Doppler angle-correction limit area where the tissue Doppler method is not valid.

Figure 12:
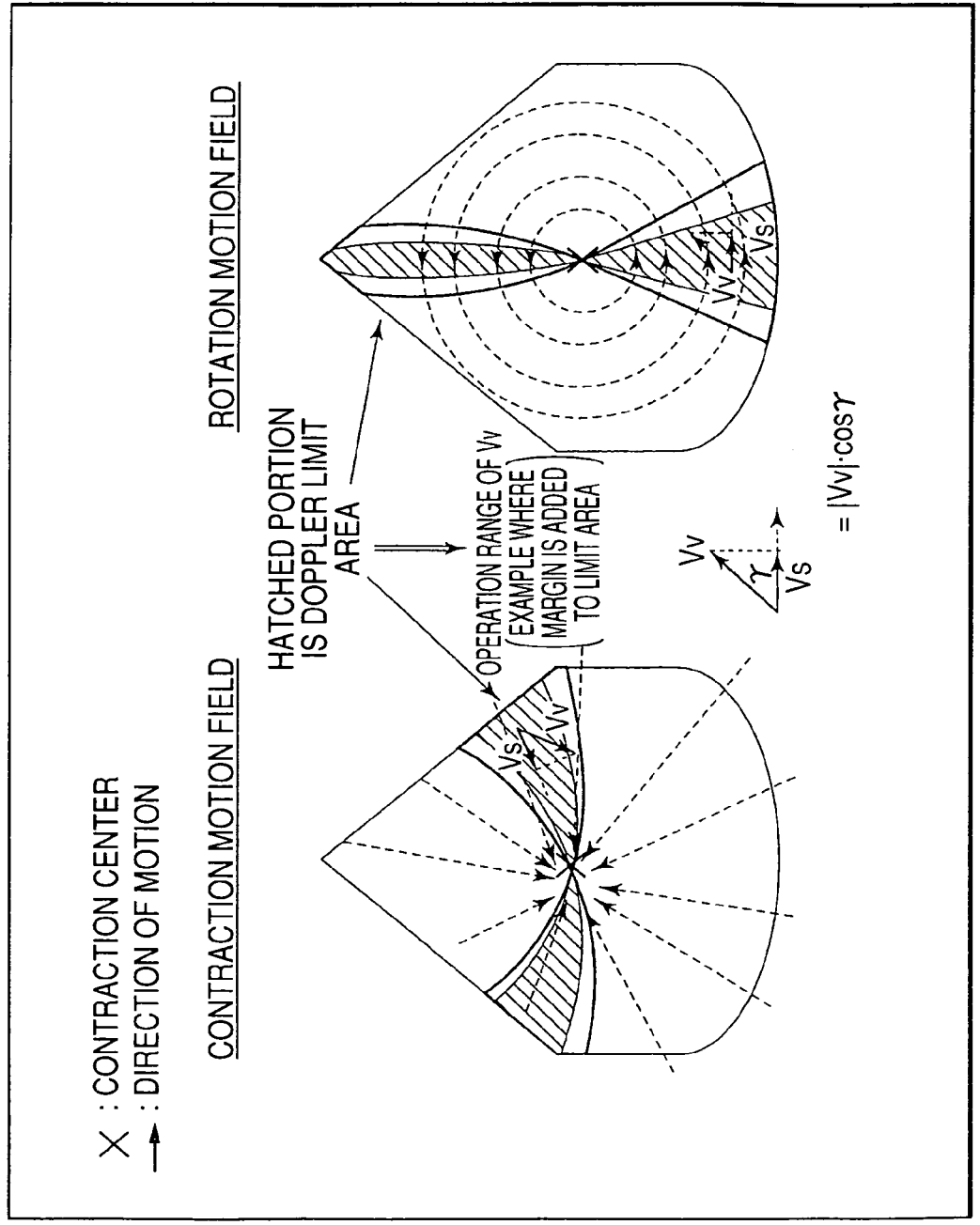
FIG. 12 is a conceptual diagram illustrating a Doppler limit area in a contraction motion field and a rotation motion field.

FIG. 12 is a diagram illustrating the Doppler limit area in the contraction motion field and the rotation motion field. In the same figure, the hatched area corresponds to the Doppler angle-correction limit area in setting the respective motion fields. That is, inside this area, since the angle θ (Doppler angle) formed by the motion direction and the scanning line arrangement direction is close to 90 degree, it is difficult to detect the velocity information with the tissue Doppler method. In the contraction motion field, for example, the area having the Doppler angle of 80 to 100 degrees (90±10 degrees) corresponds to the Doppler angle-correction limit area.

Accordingly, in the ultrasonic diagnostic instrument 10, in addition to generating the velocity distribution image Vd based on the ultrasonic image data obtained by the tissue Doppler method, the pattern matching process is performed at least inside the Doppler angle-correction limit area and two-dimensional vector velocity information is obtained from a plurality of points of a tissue.

The Doppler angle-correction limit area is not limited to the Doppler angle of 80 to 100 degrees (90±10 degrees) of the above example and may have the range of Doppler angle of 75 to 105 degree (90±15 degree) to have a more margin.

<Correcting an Angle of a Velocity (Scalar) Inside the Doppler Angle-Correction Limit Area>

Inside the Doppler angle-correction limit area, the velocity distribution image can be generated using the method according to the second embodiment. However, as shown in FIG. 12, in most area, velocities of scalar are calculated by the tissue Doppler processing unit 15 of FIG. 11. Therefore, the vector velocity information Vv inside the Doppler angle-correction limit area can be used as a tissue velocity after being converted into a scalar Vs having a component in the motion direction.

$$Vs=|Vv|\cdot\cos\gamma \qquad (11)$$

where γ is an angle formed by the vector Vv and the set motion direction.

Further, a difference in velocity value due to the difference between the calculation methods in the boundary of the area may be generated as a step difference. According to this method, since both values of Vs and Vd exist in the boundary areas (Doppler angle of 75 to 80 degrees and 100 to 105 degrees) obtained with a margin, it is also possible to reduce such a step difference by performing a weighting average expressed as the following equation (12) to the values at a Doppler angle θd to calculate Vd' and using Vd' as velocity information in the boundary area.

$$Vd'=k\cdot Vd+(1-k)\cdot Vs \qquad (12)$$

where k is a parameter which is increased as θd is more apart from 90 degree and is decreased as θd is closer to 90 degree within a range of 0≦k≦1.

<Synthesizing Images>

The above-mentioned process is performed to the velocity distribution images obtained through the above processes, thereby generating the motion information images inside and outside the Doppler angle-correction limit area. The motion information processing unit 16 synthesizes the motion information images into one synthesis image. The generated synthesis image is displayed as a motion information image of a final result in the display unit 18.

Through the respective processes described above, the output image display of characteristic quantities of the tissue motion in the supposed motion direction, which the translation velocity component has been removed and an error has been reduced in accordance with the first and second embodiments, is obtained without the Doppler angle limit and through operations for a relatively short time.

(Display Function)

Next, several display functions for effectively observing the motion information image in the ultrasonic diagnostic instrument 10 will be described. These display functions are performed by the display unit 18 and can be also embodied in the first and second embodiments.

<Display Function Using a Contraction Center as a Reference>

According to this display function, when a plurality of motion information images is displayed continuously, for example, in time series and dynamically, a contraction center is fixed at a predetermined reference position on a screen, the contraction centers of the respective images are matched with the reference position, then the respective motion information images are displayed. This is physically equivalent to observation of a heart in a state in which an observation system is set on the heart. Therefore, an observer can see images of the heart as if he rises on the heart and observes the heart. As a result, even when the position of the whole heart is temporally moved due to a translation motion, it is possible to display the heart as if it were fixed without the translation motion and to easily observe the contraction and expansion state of the heart as a detection target.

<Explicitly Displaying a Position of a Contraction Center>

As an example of clinical applicability of contraction center position information, it is described in a document entitled "Tissue Locus Imaging Compensating for Tissue Doppler Imaging in Evaluating Motion of Left Ventricle Wall" by Takenaka et el, Toshiba Medical Review Vol. 70: 51-55, 1998, that in an example of dilated cardiomyopathy, as the contraction becomes worse and the expansion degree of the left ventricle becomes increased in comparison with a normal example, the position of the contraction center is moved to a bottom of a heart in a cross section in the left ventricle major axis by a cardiac apex approach.

In view of this document, the ultrasonic diagnostic instrument 10 has a function of explicitly displaying the position of a contraction center as clinical information.

Figure 13A:
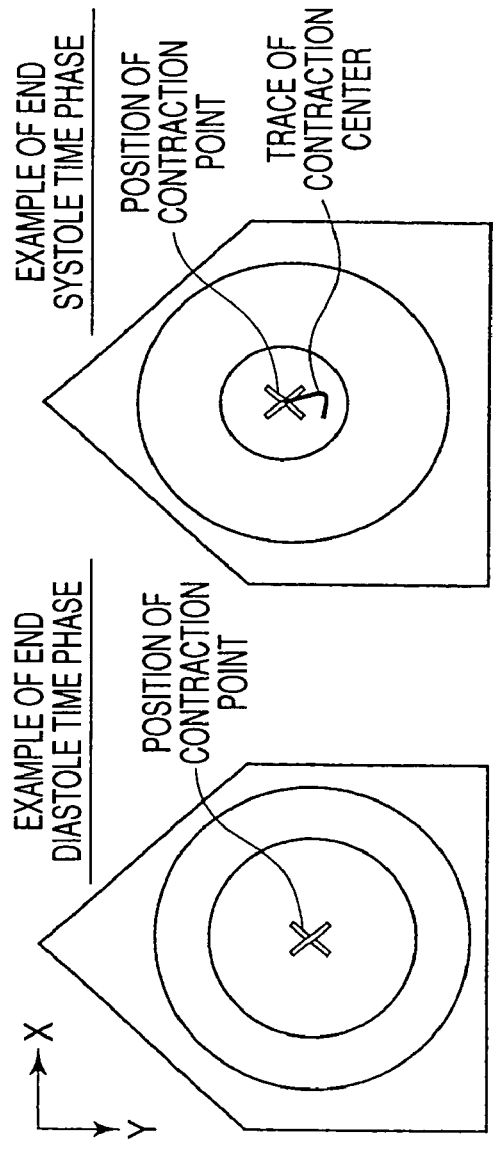
FIGS. 13A, 13B, and 13C are diagrams illustrating an example where a contraction center position is explicitly marked.
Figure 13B:
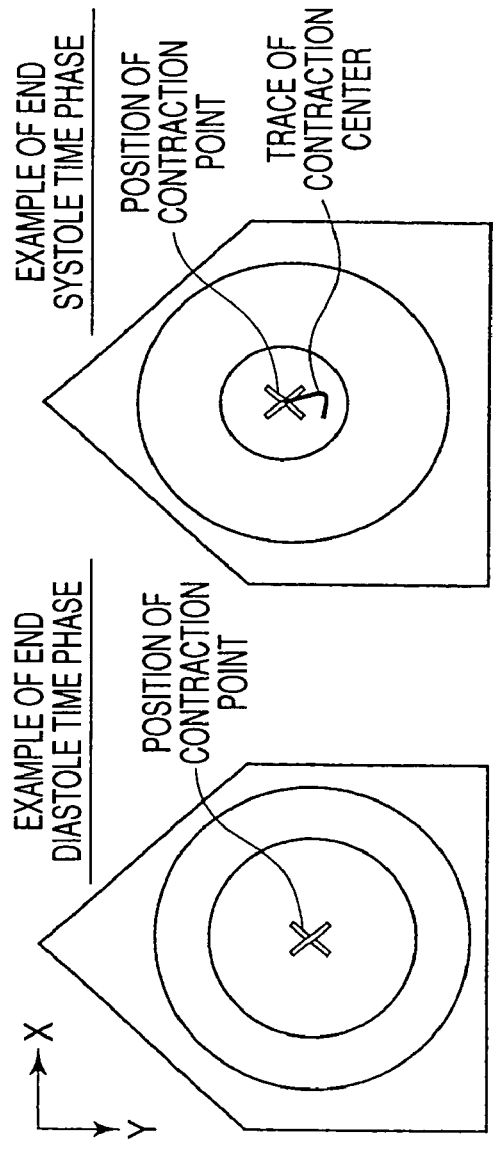
Figure 13C:
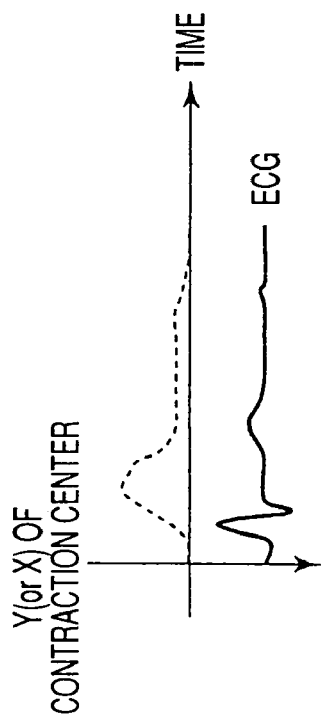

FIGS. 13A, 13B, and 13C are diagrams illustrating examples of explicitly displaying a contraction center position, respectively. That is, in FIG. 13A, the position of the contraction center is explicitly displayed by a mark X on the image. In FIG. 13B, the trace of the contraction center is explicitly displayed by a solid line on the image so as to show temporal variation in position of the contraction center. In FIG. 13C, temporal variation of the motion information (for example, displacement) of the contraction center is displayed by overlapping the image or separating a graph from the image.

In this way, by explicitly displaying the position of the contraction center as clinical information, it is possible to contribute to diagnosis support.

(Modification of TTI (Tissue Tracking Imaging) Interpolation Process Function for an Applied Image Format)

Next, a modification of the TTI interpolation process function of the ultrasonic diagnostic instrument 10 will be described. This function may be also embodied in the first and second embodiments.

Figure 14:
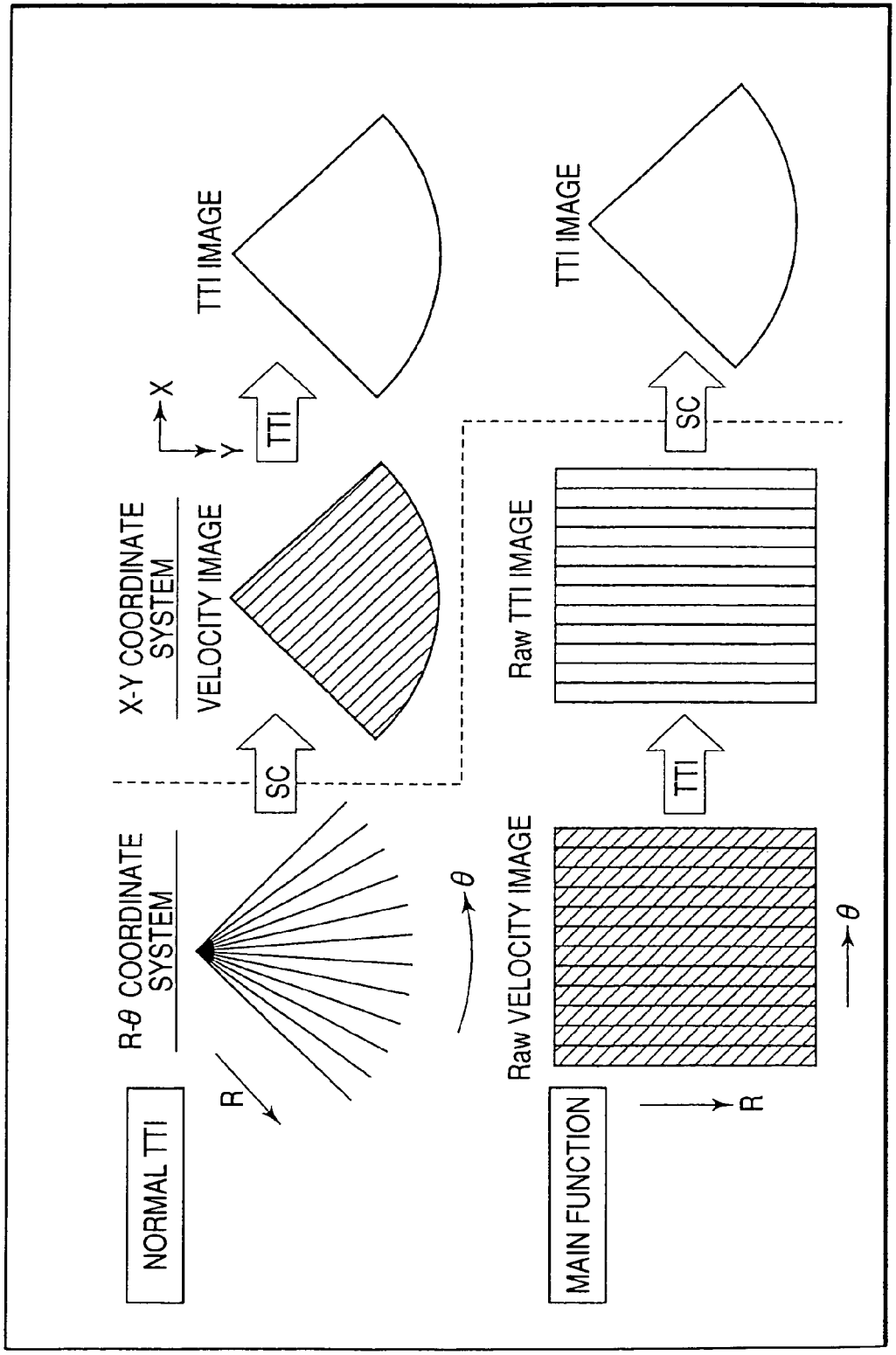
FIG. 14 is a diagram illustrating a TTI interpolation function of the ultrasonic diagnostic apparatus 10.

As shown in the upper side of FIG. 14, the normal TTI is performed using the velocity image (X-Y coordinate system) after a scan conversion (SC) process. However, the TTI may be applied to a so-called raw image (R-θ coordinate system) before the SC process. In this case, after the TTI image operation is performed on the raw image, the final image is output through the SC process.

Although it is not basically concerned whether the angle correction is performed or not, for example, as shown in the lower side of FIG. 14, when "a raster motion field (a motion field parallel to the scanning line)" is set as the motion field for the purpose of simplification, it is possible to simply acquire the motion information image through the TTI without the angle correction of the raw image.

Clinically, when the shortening of a local cardiac muscle of the left ventricle is observed using the cross section of the left ventricle of 4CH or 2CH in the major axis direction, etc. by means of the cardiac apex approach, this function is effective to some extent. This is because the motion direction of the interesting area can be substantially parallel to the scanning line depending upon the setting of the cross section. However, much attention should be paid to a case where the interesting area has a large restriction and a case where it is difficult to establish points and cross sections.

Although the present invention has been explained based on the respective embodiments described above, it will be obvious to those skilled in the art that various modifications and changes may be made thereto and it should be considered that the modifications and changes do not depart from the scope of the present invention. For example, as in (1) to (4) described below, various modifications can be made without changing the gist of the present invention.

(1) In the above embodiments, it has been described that received signals constituting the ultrasonic data are obtained two-dimensionally. However, without being limited to the two dimensions, the present invention may be also applied through expansion of dimensions to a case where the same received signals are obtained three-dimensionally.

(2) In the above embodiments, the ultrasonic diagnostic instrument 10 has been exemplified. However, without being limited to ultrasonic diagnostic instrument, a series of processes described above may be performed separately from the ultrasonic diagnostic instrument by using a personal computer, a workstation, or other computers having the same function.

(3) In the second embodiment, the detection of the so-called thickening component in the minor axis direction of a heart has been described. However, without being limited to the detection of the thickening component, the present invention may be applied to the detection of a so-called shortening component in a major axis direction of the heart.

In this case, it is ideal that the motion field is set along a cardiac muscle of a major axis direction, but the rotation motion field may be set for the purpose of simplification. This is because this motion component (approximately) corresponds to the shortening component and only the shortening component can be provided without influence of the rotation motion component by removing the thickening component of the direction (contraction motion direction) perpendicular to this motion component.

(4) In the above embodiments, time analysis techniques after forming the motion information image is not described. However, for example, the time analysis described in Japanese Patent Application No. 2002-272845 may be applied and by applying the time analysis technique in a state in which the accuracy of the motion information image is enhanced through the techniques of the above embodiments, it is possible to provide a time analysis result with higher accuracy.

The present invention is not limited to the above-mentioned embodiments, but the constituent elements may be modified and embodied without departing from the gist of each process. Various aspects of the present invention may be put into practice by properly combining a plurality of constituent elements in the above-mentioned embodiments. For example, some constituent elements may be omitted in any one embodiment described above. Further, the constituent elements of the different embodiments may be properly combined.

What is claimed is:

1. An ultrasonic image processor comprising:
    a storage unit for storing a plurality of ultrasonic data acquired at a plurality of time phases of a heart of a sample;
    a motion field setting unit for setting a motion field defining a motion direction of the heart for the plurality of ultrasonic data;
    a contraction center setting unit for setting a contraction center of the heart for the plurality of ultrasonic data;
    a first distribution image generating unit for generating a first distribution image of a motion velocity in the motion direction defined by the motion field every time phase on the basis of the plurality of ultrasonic data;
    a first estimation unit for estimating a translation motion component of the heart based on the contraction center of the heart at least two continuous time phases;
    a second distribution image generating unit for generating a second distribution image every time phase by correcting the plurality of first distribution images on the basis of the translation motion component;
    a tracking point setting unit for setting a plurality of tracking points existing in a tissue region of the sample on a second distribution image at a predetermined time phase among the plurality of second distribution images;
    a second estimation unit for estimating corresponding points corresponding to the plurality of tracking points at each time phase on the basis of velocities of the plurality of tracking points and time intervals between the plurality of time phases in the plurality of second distribution images corresponding to the other time phases other than the predetermined time phase;

a signal value determining unit for determining signal values of the tracking points and the corresponding points on the basis of the second distribution image at each time phase;

a motion information image generating unit for generating a motion information image on the basis of the signal values of the tracking points and the corresponding points; and a display unit for displaying the motion information image.

2. The ultrasonic image processor according to claim 1, wherein the plurality of ultrasonic data includes at least one of B mode image data and ultrasonic received signal data for obtaining the B mode image, and the first distribution image generating unit generates the plurality of motion velocity distribution images by performing a pattern matching process between adjacent time phases to the plurality of ultrasonic data.

3. The ultrasonic image processor according to claim 1, wherein the ultrasonic data are image data acquired in the tissue Doppler mode.

4. The ultrasonic image processor according to claim 1, further comprising a third estimation unit for estimating a rotation motion component of the heart which is a motion component having a direction substantially perpendicular to the translation motion component on the basis of the plurality of first distribution images, wherein the second distribution image generating unit generates a plurality of second distribution images by correcting the plurality of first distribution images on the basis of the translation motion component and the rotation motion component.

5. The ultrasonic image processor according to claim 1, wherein the motion field setting unit sets the motion field to a vector field toward the contraction center of the heart.

6. The ultrasonic image processor according to claim 1, wherein the contraction center setting unit:

when ultrasonic data of front and rear time phases of an arbitrary time phase exists, sets the contraction center using a linear interpolation process based on the ultrasonic data of the front and rear time phases, when only the ultrasonic data of the front time phase exists, sets the contraction center on the basis of only the ultrasonic data of the front time phase, and when only the ultrasonic data of the rear time phase exists, sets the contraction center on the basis of only the ultrasonic data of the rear time phase.

7. The ultrasonic image processor according to claim 1, wherein the contraction center setting unit:

automatically detects an endocardium position of the heart using the plurality of ultrasonic data, extracts cardiac chamber area information at each time phase, and estimates and sets the position of the contraction center at each time phase from the cardiac chamber area information at each time phase.

8. The ultrasonic image processor according to claim 1, wherein the motion information image is one of a velocity image, a distortion image, a displacement image, and a distortion velocity image.

9. The ultrasonic image processor according to claim 1, wherein when continuously displaying a plurality of the motion information images, the display unit displays the motion information images after matching the contraction centers of the motion information images to one another.

10. The ultrasonic image processor according to claim 1, wherein the display unit displays at least one of graphs indicating the contraction center, a trace of the contraction center, and temporal variation of position movement information of the contraction center on the motion information image.

11. The ultrasonic image processor according to claim 1, wherein the plurality of ultrasonic data is raw image data of the polar coordinate system based on a position of a scanning line of an ultrasonic wave, and the motion information image generating unit converts the raw image data of the polar coordinate system into an image of the orthogonal coordinate system and generates the motion information image as a scan conversion image.

12. An ultrasonic image processor, comprising:

a storage unit for storing first ultrasonic data as a tissue image radiographed in a tissue Doppler mode at each of a plurality of time phases of a heart of a sample and second ultrasonic data as a tissue image radiographed in a radiography mode other than the tissue Doppler mode at each of the plurality of time phases;

a motion field setting unit for setting a motion field defining a motion direction of the heart for the plurality of first ultrasonic data and the plurality of second ultrasonic data;

a contraction center setting unit for setting a contraction center of the heart for the plurality of first ultrasonic data and the plurality of second ultrasonic data;

a distribution image generating unit for generating a first distribution image of a motion velocity toward the contraction center every time phase on the basis of the plurality of first ultrasonic data and generating a second distribution image of a motion velocity toward the contraction center every time phase on the basis of the plurality of second ultrasonic data;

a first estimation unit for estimating a translation motion component of the heart based on the contraction center of the heart at least two continuous time phases;

a corrected distribution-image generating unit for generating a first corrected distribution image every time phase by correcting a plurality of the first distribution images on the basis of the translation motion component and generating a second corrected distribution image every time phase by correcting a plurality of the second distribution images on the basis of the translation motion component;

a motion information image generating unit for generating a motion information image using the first corrected distribution image and the second corrected distribution image; and a display unit for displaying the motion information image.

13. The ultrasonic image processor according to claim 12, wherein the motion information image generating unit:

sets a plurality of tracking points existing in a tissue region of the sample in the first corrected distribution image and the second corrected distribution image corresponding to at least one time phase, tracks corresponding points corresponding to the plurality of tracking points every time phase in the first corrected distribution image and the second corrected distribution image at the other time phases other than the at least one time phase on the basis of motion velocities of the plurality of tracking points and time intervals between the plurality of time phases, determines signal values of the tracking points and the corresponding points on the basis of the first corrected distribution image and the second corrected distribution image at each time phase, and generates the motion information image on the basis of the signal values of the tracking points and the corresponding points.

14. The ultrasonic image processor according to claim 12, wherein the motion information image generating unit:

generates the motion information image using the first corrected distribution image in an area where a Doppler angle correction is valid, and generates the motion information image using the second corrected distribution image in an area where the Doppler angle correction is not valid.

15. The ultrasonic image processor according to claim 12, wherein the first estimation unit estimates a rotation motion component of the heart which is a motion component having a direction substantially perpendicular to the translation motion component on the basis of the plurality of second ultrasonic data, and the corrected distribution-image generating unit generates the second corrected distribution image every time phase by correcting the plurality of second distribution images on the basis of the translation motion component and the rotation motion component.

16. The ultrasonic image processor according to claim 12, wherein the motion field setting unit sets the motion field to a vector field toward the contraction center of the heart.

17. The ultrasonic image processor according to claim 12, wherein the contraction center setting unit:

when ultrasonic data of front and rear time phases of an arbitrary time phase exists, sets the contraction center using a linear interpolation process based on the ultrasonic data of the front and rear time phases, when only the ultrasonic data of the front time phase exists, sets the contraction center on the basis of only the ultrasonic data of the front time phase, and when only the ultrasonic data of the rear time phase exists, sets the contraction center on the basis of only the ultrasonic data of the rear time phase.

18. The ultrasonic image processor according to claim 12, wherein the contraction center setting unit:

automatically detects an endocardium position of the heart using the plurality of ultrasonic data, extracts cardiac chamber area information at each time phase, and estimates and sets the position of the contraction center at each time phase from the cardiac chamber area information at each time phase.

19. The ultrasonic image processor according to claim 12, wherein the motion information image is one of a velocity image, a distortion image, a displacement image, and a distortion velocity image.

20. The ultrasonic image processor according to claim 12, wherein when continuously displaying a plurality of the motion information images, the display unit displays the motion information images after matching the contraction centers of the motion information images to one another.

21. The ultrasonic image processor according to claim 12, wherein the display unit displays at least one of graphs indicating the contraction center, a trace of the contraction center, and temporal variation of position movement information of the contraction center on the motion information image.

22. The ultrasonic image processor according to claim 12, wherein the plurality of ultrasonic data is raw image data of the polar coordinate system based on a position of a scanning line of an ultrasonic wave, and the motion information image generating unit converts the raw image data of the polar coordinate system into an image of the orthogonal coordinate system and generates the motion information image as a scan conversion image.

23. An ultrasonic image processor, comprising:

a storage unit for storing a plurality of ultrasonic data acquired at a plurality of time phases of a heart of a sample;

a motion field setting unit for setting a motion direction of the heart for the plurality of ultrasonic data;

a contraction center setting unit for setting a contraction center of the heart for the plurality of ultrasonic data;

a first distribution image generating unit for generating a first distribution image of a motion velocity toward the contraction center along the motion direction every time phase on the basis of the plurality of ultrasonic data;

a first estimation unit for estimating a translation motion component of the heart on the basis of the contraction center of the heart at least two continuous time phases;

a second distribution image generating unit for generating a second distribution image every time phase by correcting a plurality of the first distribution images on the basis of the translation motion component;

a tracking point setting unit for setting a plurality of tracking points existing in a tissue region of the sample on the second distribution image at a predetermined time phase among the plurality of second distribution images;

a second estimation unit for estimating corresponding points corresponding to the plurality of tracking points at each time phase on the basis of motion velocities of the plurality of tracking points and time intervals between the plurality of time phases in the plurality of second distribution images corresponding to the other time phases other than the predetermined time phase;

a signal value determining unit for determining signal values of the tracking points and the corresponding points on the basis of the second distribution image at each time phase;

a motion information image generating unit for generating a motion information image on the basis of the signal values of the tracking points and the corresponding points; and a display unit for displaying the motion information image.

24. An ultrasonic image processor, comprising:

a storage unit for storing first ultrasonic data as a tissue image radiographed in a tissue Doppler mode at each of a plurality of time phases of a heart of a sample and second ultrasonic data as a tissue image radiographed in a radiography mode other than the tissue Doppler mode at each time phases;

a motion field setting unit for setting a motion direction of the heart for the plurality of first ultrasonic data and the plurality of second ultrasonic data;

a contraction center setting unit for setting a contraction center of the heart for the plurality of first ultrasonic data and the plurality of second ultrasonic data;

a distribution image generating unit for generating a first distribution image of a motion velocity toward the contraction center along the motion direction every time phase on the basis of the plurality of first ultrasonic data and generating a second distribution image of a motion velocity toward the contraction center every time phase on the basis of the plurality of second ultrasonic data;

a first estimation unit for estimating a translation motion component of the heart based on the contraction center of the heart at least two continuous time phases;

a corrected distribution-image generating unit for generating a first corrected distribution image every time phase by correcting a plurality of the first distribution images on the basis of the translation motion component and generating a second corrected distribution image every time phase by correcting a plurality of the second distribution images on the basis of the translation motion component;

a motion information image generating unit for generating a motion information image using the first corrected distribution image and the second corrected distribution image; and a display unit for displaying the motion information image.

25. An ultrasonic diagnostic instrument comprising:

an ultrasonic probe for transmitting an ultrasonic wave to an area including a heart of a sample and receiving an echo signal from the sample;

a driving signal generating unit for generating a driving signal driving the ultrasonic probe and applying the driving signal to the ultrasonic probe at each of a plurality of time phases of the heart of the sample;

a data generating unit for generating a plurality of ultrasonic data on the basis of the echo signal received through the ultrasonic probe from the area at each of the plurality of time phases;

a motion field setting unit for setting a motion field defining a motion direction of the heart for the plurality of ultrasonic data;

a contraction center setting unit for setting a contraction center of the heart for the plurality of ultrasonic data;

a first distribution image generating unit for generating a first distribution image of a motion velocity in the motion direction defined by the motion field every time phase on the basis of the plurality of ultrasonic data;

a first estimation unit for estimating a translation motion component of the heart on the basis of the contraction center of the heart at least two continuous time phases;

a second distribution image generating unit for generating a second distribution image every time phase by correcting a plurality of the first distribution images on the basis of the translation motion component;

a tracking point setting unit for setting a plurality of tracking points existing in a tissue region of the sample on a second distribution image at a predetermined time phase among the plurality of second distribution images;

a second estimation unit for estimating corresponding points corresponding to the plurality of tracking points at each time phase on the basis of velocities of the plurality of tracking points and time intervals between the plurality of time phases in the plurality of second distribution images corresponding to the other time phases other than the predetermined time phase;

a signal value determining unit for determining signal values of the tracking points and the corresponding points on the basis of the second distribution image at each time phase;

a motion information image generating unit for generating a motion information image on the basis of the signal values of the tracking points and the corresponding points; and a display unit for displaying the motion information image.

26. An ultrasonic diagnostic instrument comprising:

a radiography unit for acquiring first ultrasonic data as a tissue image in a tissue Doppler mode at each of a plurality of time phases of a heart of a sample and second ultrasonic data as a tissue image in a radiography mode other than the tissue Doppler mode at each of the plurality of time phases;

a motion field setting unit for setting a motion field defining a motion direction of the heart for the plurality of first ultrasonic data and the plurality of second ultrasonic data;

a contraction center setting unit for setting a contraction center of the heart for the plurality of first ultrasonic data and the plurality of second ultrasonic data;

a distribution image generating unit for generating a first distribution image of a motion velocity toward the contraction center every time phase on the basis of the plurality of first ultrasonic data and generating a second distribution image of a motion velocity toward the contraction center every time phase on the basis of the plurality of second ultrasonic data;

a first estimation unit for estimating a translation motion component of the heart based on the contraction center of the heart at least two continuous time phases;

a corrected distribution-image generating unit for generating a first corrected distribution image every time phase by correcting a plurality of the first distribution images on the basis of the translation motion component and generating a second corrected distribution image every time phase by correcting a plurality of the second distribution images on the basis of the translation motion component;

a motion information image generating unit for generating a motion information image using the first corrected distribution image and the second corrected distribution image; and a display unit for displaying the motion information image.

27. An ultrasonic image processing method performed by an ultrasonic image processor, comprising:

setting a motion field defining a motion direction of a heart for a plurality of ultrasonic data acquired at each of a plurality of time phases of the heart of a sample;

setting a contraction center of the heart for the plurality of ultrasonic data;

generating a first distribution image of a motion velocity in the motion direction defined by the motion field every time phase on the basis of the plurality of ultrasonic data;

estimating a translation motion component of the heart on the basis of the contraction center of the heart at least two continuous time phases;

generating a second distribution image every time phase by correcting the plurality of first distribution images on the basis of the translation motion component;

setting a plurality of tracking points existing in a tissue region of the sample on the second distribution image at a predetermined time phase among the plurality of second distribution images;

estimating corresponding points corresponding to the plurality of tracking points at each time phase on the basis of velocities of the plurality of tracking points and time intervals between the plurality of time phases in the plurality of second distribution images corresponding to the other time phases other than the predetermined time phase;

determining signal values of the tracking points and the corresponding points on the basis of the second distribution image at each time phase; and
generating a motion information image on the basis of the signal values of the tracking points and the corresponding points.

28. An ultrasonic image processing method performed by an ultrasonic image processor, comprising:
setting a motion field defining a motion direction of a heart for first ultrasonic data as a tissue image radiographed in a tissue Doppler mode at each of a plurality of time phases of the heart of a sample and second ultrasonic data as a tissue image radiographed in a radiography mode other than the tissue Doppler mode at each of the plurality of time phases;
setting a contraction center of the heart for a plurality of the first ultrasonic data and a plurality of the second ultrasonic data;
generating a first distribution image of a motion velocity toward the contraction center every time phase on the basis of the plurality of first ultrasonic data and generating a second distribution image of a motion velocity toward the contraction center every time phase on the basis of the plurality of second ultrasonic data;
estimating a translation motion component of the heart based on the contraction center of the heart at at least two continuous time phases;
generating a first corrected distribution image every time phase by correcting a plurality of the first distribution images on the basis of the translation motion component and generating a second corrected distribution image every time phase by correcting a plurality of the second distribution images on the basis of the translation motion component; and
generating a motion information image using the first corrected distribution image and the second corrected distribution image.

29. A non-transitory computer-readable memory including instructions which when executed by a computer cause the computer to:
set a motion field defining a motion direction of a heart for a plurality of ultrasonic data acquired at each of a plurality of time phases of the heart of a sample;
set a contraction center of the heart for the plurality of ultrasonic data;
generate a first distribution image of a motion velocity in the motion direction defined by the motion field every time phase on the basis of the plurality of ultrasonic data;
estimate a translation motion component of the heart on the basis of the contraction center of the heart at least two continuous time phases;
generate a second distribution image every time phase by correcting the plurality of first distribution images on the basis of the translation motion component;
set a plurality of tracking points existing in a tissue region of the sample on the second distribution image at a predetermined time phase among the plurality of second distribution images;
estimate corresponding points corresponding to the plurality of tracking points at each time phase on the basis of velocities of the plurality of tracking points and time intervals between the plurality of time phases in the plurality of second distribution images corresponding to the other time phases other than the predetermined time phase;
determine signal values of the tracking points and the corresponding points on the basis of the second distribution image at each time phase;
generate a motion information image on the basis of the signal values of the tracking points and the corresponding points; and
display the motion information image.

30. A non-transitory computer-readable memory including instructions which when executed by a computer cause the computer to:
set a motion field defining a motion direction of a heart for first ultrasonic data as a tissue image radiographed in a tissue Doppler mode at each of a plurality of time phases of the heart of a sample and second ultrasonic data as a tissue image radiographed in a radiography mode other than the tissue Doppler mode at each of the plurality of time phases;
set a contraction center of the heart for a plurality of the first ultrasonic data and a plurality of the second ultrasonic data;
generate a first distribution image of a motion velocity toward the contraction center every time phase on the basis of the plurality of first ultrasonic data and to generate a second distribution image of a motion velocity toward the contraction center every time phase on the basis of the plurality of second ultrasonic data;
estimate a translation motion component of the heart based on the contraction center of the heart at least two continuous time phases;
generate a first corrected distribution image every time phase by correcting a plurality of the first distribution images on the basis of the translation motion component and to generate a second corrected distribution image every time phase by correcting a plurality of the second distribution images on the basis of the translation motion component;
generate a motion information image using the first corrected distribution image and the second corrected distribution image; and
display the motion information image.

* * * * *

UNITED STATES PATENT AND TRADEMARK OFFICE
CERTIFICATE OF CORRECTION

PATENT NO. : 7,837,625 B2  
APPLICATION NO. : 10/968095  
DATED : November 23, 2010  
INVENTOR(S) : Yasuhiko Abe Page 1 of 1

It is certified that error appears in the above-identified patent and that said Letters Patent is hereby corrected as shown below:

On the title page, Item (73), the 2$^{nd}$ Assignee's name is incorrect. Item (73) should read:

-- (73) Assignees: Kabushiki Kaisha Toshiba, Tokyo (JP);  
Toshiba Medical Systems Corporation,  
Otawara-shi (JP) --

Signed and Sealed this  
Eighteenth Day of January, 2011

David J. Kappos  
*Director of the United States Patent and Trademark Office*